United States Patent [19]

Anderson

[11] Patent Number: 4,873,346

[45] Date of Patent: Oct. 10, 1989

[54] SUBSTITUTED BENZOTHIAZOLES, BENZIMIDAZOLES, AND BENZOXAZOLES

[75] Inventor: David J. Anderson, Portage, Mich.

[73] Assignee: The Upjohn Company, Kalamazoo, Mich.

[21] Appl. No.: 778,340

[22] Filed: Sep. 20, 1985

[51] Int. Cl.$^4$ .................. C07D 417/12; C07D 277/74
[52] U.S. Cl. ..................................... 548/157; 548/159; 548/160; 548/161; 548/165; 548/169; 548/170; 548/173; 548/221; 548/222; 548/327; 548/328; 548/329
[58] Field of Search ............... 548/157, 159, 160, 161, 548/165, 170, 169, 173

[56] References Cited

U.S. PATENT DOCUMENTS

| | | | |
|---|---|---|---|
| 2,769,010 | 10/1956 | D'Amico | 548/157 |
| 3,704,239 | 11/1972 | Webe | 99/8 |
| 3,715,363 | 2/1973 | Diekman | 548/165 |
| 3,775,426 | 11/1973 | Wei et al. | 548/329 |
| 3,849,431 | 11/1974 | Gallay et al. | 260/306.6 R |
| 3,934,017 | 1/1976 | Gallay et al. | 424/270 |
| 3,985,762 | 10/1976 | Dransch et al. | 260/306 |
| 4,216,160 | 8/1980 | Dorn et al. | 260/455 R |
| 4,294,839 | 10/1981 | Doll et al. | 424/263 |
| 4,328,219 | 5/1982 | Mues et al. | 548/152 |
| 4,329,363 | 5/1982 | Dorn et al. | 424/320 |
| 4,340,738 | 7/1982 | Sipido | 548/151 |
| 4,612,049 | 9/1986 | Berner et al. | 106/14 |
| 4,696,763 | 9/1987 | Bentley et al. | 548/171 |
| 4,719,036 | 1/1988 | Clubley et al. | 548/165 |

FOREIGN PATENT DOCUMENTS

| | | |
|---|---|---|
| 633672 | 6/1962 | Belgium . |
| 754874 | 10/1969 | Belgium . |
| 0001989A1 | 5/1979 | European Pat. Off. . |
| 0006347A1 | 1/1980 | European Pat. Off. . |
| 2135543 | 7/1971 | Fed. Rep. of Germany ......... 91/28 |
| 2355092 | 5/1975 | Fed. Rep. of Germany . |
| 2913527 | 10/1980 | Fed. Rep. of Germany . |
| 3207640A1 | 3/1982 | Fed. Rep. of Germany . |
| 1476558 | 7/1965 | France . |
| 1508322 | 1/1968 | France . |
| 1509192 | 1/1968 | France . |
| 156830 | 11/1967 | Hungary . |
| 1205/69 | 7/1965 | Japan . |
| 49013172 | 6/1972 | Japan . |
| 49044040 | 9/1972 | Japan . |
| 74041198 | 11/1974 | Japan . |
| 54003064 | 6/1977 | Japan .................................. 277/74 |
| 54066673 | 11/1977 | Japan .................................. 263/58 |
| 4003064 | 1/1979 | Japan .................................. 548/170 |
| 57042607 | 8/1980 | Japan .................................. 277/70 |
| 57120582 | 1/1981 | Japan .................................. 277/82 |
| 6803271 | 3/1967 | Netherlands . |
| 6903957 | 8/1968 | Netherlands ........................ 49/38 |
| 2100262A | 6/1981 | United Kingdom . |

OTHER PUBLICATIONS

R. A. Glennon et al., Benz–Fused Mesoionic Xanthine Analogues as Inhibitors of Cyclic-AMP Phosphodiesterase, J. Med. Chem. 24: 766–69 (1981).

P. T. S. Lau and T. E. Gompft, Reaction of Quinones with Thiourea, J. Org. Chem. 35:4103–08 (1970).

G. Foscolos et al., (not translated), Prakt. Akad. Athenon 51:274–91 (1976).

K. Tanaka et al., Cyclization of [(4– or 5–Substituted-2-Benzimidazolyl)thio]Acetic Acids, Chem. Pharm. Bull. 29:1876–86 (1981).

H. O. Hankovszky et al., Benzazoles, V., The Preparation of 2-(N-Arylideneamino)benzazoles and 2-(-N-Arylideneneaminomethyl)benzimidazoles and Their Reduction with Sodium Borohydride, Acta Chimica Academiae Scientiarum Hungaricae Tomus 53:405–16 (1967).

M. Patra et al., J. Indian Chem. Soc., vol. LV, Jun. 1978, pp. 587–588.

J. D'Amico et al., J. Am. Chem. Soc. 81, 5957–63 (1959).

Primary Examiner—Mary E. Ceperley
Attorney, Agent, or Firm—Martha A. Cox; Donald L. Corneglio

[57] ABSTRACT

The present invention provides certain novel substituted benzothiazoles, benzimidazoles and benzoxazoles which are useful as inhibitors of leukotriene biosynthesis and/or as inhibitors of the action of lipoxygenase and/or as inhibitors of mucus secretion in mammalian metabolism. They are thus employed wherever it is medically necessary or desirable to inhibit these systems.

5 Claims, No Drawings

SUBSTITUTED BENZOTHIAZOLES, BENZIMIDAZOLES, AND BENZOXAZOLES

BACKGROUND OF THE INVENTION

The present invention provides novel compositions of matter. In particular, the present invention provides novel substituted benzothiazoles, benzimidazoles and benzoxazoles which are useful as inhibitors of the synthesis of leukotrienes and/or as inhibitors of the action of 5-lipoxygenase in mammalian metabolism.

The leukotrienes are a class of unsaturated fatty acid compounds which are derived from arachidonic acid by the action of lipoxygenase. See, e.g., Samuelsson, Trends in Pharmacological Sciences, 5:227 (1980); and Samuelsson, et al., Annu. Rev. Biochem. 47:997–1029 (1978). For a discussion of leukotriene nomenclature, see Samuelsson, et al., Prostaglandins, 19:645 (1980).

The leukotrienes have been discovered as potent constrictors of human bronchi. That is, certain leukotrienes are mediators of the action of slow-reacting substance of anaphylaxis (SRS-A). See, e.g., Dahlen, Nature, 288:484 (1980). These compounds are therefore important mediators of bronchoconstriction in humans.

The role of leukotrienes as agonists in immediate hypersensitivity and other pathological conditions has led to research into inhibitors of leukotriene biosynthesis and leukotriene antagonists. See, e.g., Corey, et al., Tet. Lett. 21:4243 (1980).

Leukotrienes, particularly leukotriene $C_4$ ($LTC_4$) and leukotriene $D_4$ ($LTD_4$) have been shown to be potent mucus secretagogues. Both $LTC_4$ and $LTD_4$ increase the release of mucus from human airways in vitro, Z. Maron, et al., Am. Rev. Respir. Dis. 126, 449–451 (1982); S. J. Coles, et al., Prostaglandins 25, 155–170 (1983), and from canine tracheas in vivo, H. G. Johnson, et al., Int. J. Immunopharmacol. 5, 178 (1983); H. G. Johnson, et al., Prostaglandins 25, 237–243 (1983). Arachidonic acid, metabolic products of arachidonic acid, monohydroxy-eicosatetraenoic acid, and prostaglandins also release mucus from human airway, Z. Maron, et al., J. Clin. Invest. 67, 1695–1702 (1981). $LTC_4$ was effective in stimulating mucus release in vivo in the cat but not in vitro on cat trachea tissue, A. C. Peatfield, et al., Br. H. Pharmac. 77, 391–393 (1982). J. H. Shelhamer, et al., Chest 81, 36S (1982) summarizes the nature of evidence available suggesting that lipoxygenase products generated by the airways in vitro might be responsible for the augmented mucus release.

O. Cromwell, et al., The Lancet, July 25, 1981, pp. 164–165, identified $LTB_4$ and $LTD_4$ in the sputum of cystic fibrosis patients and speculated, therefore, that inhibitors of the lipoxygenase pathway might be capable of reversing the airway obstruction in such patients.

T. Ahmed, et al., Am. Rev. Respir. Dis. 124, 110–114 (1981) demonstrated that FPL 55712, an $LTC_4$ antagonist when given prior to antigen challenge was effective in reversing the tracheal mucus velocity in patients with a history of bronchial asthma but concluded that the clinical significance of FPL 55712 remains to be demonstrated.

In mammalian metabolism, arachidonic acid is transformed to 12-L-hydroperoxy-5,8,10,14-eicosatetraenoic acid by the action of 12-lipoxygenase. See, Hamberg, et al., Proc. Nat. Acad. Sci. 71:3400–3404 (1974). Similarly, 5-lipoxygenase transforms arachidonic acid into 5-S-hydroperoxy-6,8,11,14-eicosatetraenoic acid. Thus, an agent which inhibits the action of lipoxygenase would be useful in treating or preventing untoward conditions associated with lipoxygenase products.

Therefore, compounds which inhibit the action of lipoxygenase are useful in the treatment of inflammatory conditions where it is desirable to prevent migration of polymorphonuclear leukocytes to the inflammatory site. They are also useful in the treatment of asthma.

Derwent Basic Abstract, Accession Number 91528R, dicloses sulphonyl- and sulphoxylalkylenerhodanines with fungicidal activity.

Derwent Basic Abstract, Accession Number 21800V, dicloses cardiac drugs prepared from corresponding 2-mercapto-benzothiazole derivatives.

Derwent Basic Abstract, Accession Number 29,700, discloses fungicidal, bactericidal alkylbenzothiazolyl sulphones.

Derwent Basic Abstract, Accession Number 00368X, discloses 2-(3-Amino-2-hydroxypropylthio)-benzothiazoles with hypotensive activity.

Derwent Basic Abstract, Accession Number 33201Y, discloses benzene sulphenamides, with heteroaryl-thio, -sulphinyl or -sulphonyl groups, which are cerebral vasodilators without hypotensive effects.

Derwent Basic Abstract, Accession Number 16714W, and Derwent Basic Abstract, Accession Number 33156C, diclose methods for preparing benzothiazolesulphenamide derivatives.

Chemical Abstracts 47:12358c discloses 2,6-substituted benzothiazoles.

Chemical Abstracts 48:4522b discloses 4-(5-, 6-, or 7-)chlorobenzthiazol-2-yl-thiomethane-carboxylic acid.

Derwent Basic Abstract, Accession Number 32993W, discloses pesticidal compositions containing benzoxazole derivatives as active agents, useful in agriculture.

Derwent Basic Abstracts, Accession Number 40,965 and 80522S, disclose methyl-1-naphthyldithiocarbamic acid-2-benzoxazolyl ester which has antimycotic use.

Derwent Basic Abstract, Accession Number 12569, discloses N'-diethylaminoethyl-2-mercapto-benzimidazole derivatives as analgesics.

Derwent Basic Abstract, Accession Number 13,360, discloses 1-($\beta$-diethylaminoethyl)-2-(p-aminophenylthio)-benzimidazole and its hydrochloride salt having analgetic uses.

Derwent Basic Abstract, Accession Number 20,701, discloses N-substituted, 2-thiol derivatives of benzimidazoles which are analgesics.

Derwent Basic Abstract, Accession Number 28,529, discloses 2-phenylthiobenzimidazoles which are analgesics and intermediates.

Derwent Basic Abstract, Accession Number 31,421, discloses pesticidal benzimidazole thiol-carbamates.

Derwent Basic Abstract, Accession Number 36097R, discloses 1-($\beta$-pyrrolidino-ethyl)-2-(p-ethoxyphenylthio)-benzimidazole as an analgesic.

Derwent Basic Abstract, Accession Number 44380R, discloses 2-methylthio-1(3'-nicotinyl)-benzimidazole as an antiinflammatory agent.

Derwent Basic Abstracts, Accession Numbers 15402U, 60320W and 17936U, disclose mercapto-benzimidazolyl (thio) ureas and 1-acyl-2-(phenylcarbamoyl-alkylthio)benzimidazoles useful as anthelmintics.

Derwent Basic Abstract, Accession Number 32075U, discloses 1-(bis-(2-chloroethyl)carbamoyl-benzimidazoles with potential cytostatic and immunosuppressant activity.

Derwent Basic Abstract, Accession Number 61208W, discloses 2-(benzimidazol-2-ylthio)succinic acids which are useful as antiinflammatory and analgesic agents and as chelating agents.

Derwent Basic Abstracts, Accession Number 68107W, 75825W, 02854Y, 02855Y, 08362Y, 08363Y and 11905Y, disclose benzimidazolyl-piperidine derivatives with psychotropic properties.

Derwent Basic Abstract, Accession Number 86748W, discloses antiinflammatory, N-substituted-mercaptobenzimidazoles.

Derwent Basic Abstract, Accession Number 74426A, discloses 2-alkylthio-5-phenoxy or phenylthio-benzimidazole derivatives which are useful in anthelmintics.

Derwent Basic Abstracts, Accession Numbers 79478B and 82975X, disclose substituted pyridyl-sulphinyl-benzimidazoles are gastric acid secretion inhibiting agents.

Derwent Basic Abstract, Accession Number 54809E, discloses pyridyl substituted 2-hydroxy or mercapto benzimidazole derivatives which are useful as cardiotonic agents.

Derwent Basic Abstract, Accession Number 27874K, discloses 2-substituted-pyridinyl methylthio-benzimidazole derivatives which are useful as inhibitors of gastric acid secretion.

Derwent Basic Abstract, Accession Number 54214K, discloses 4-methoxy-2-pyridylmethyl)thio- and -sulphinyl benzimidazole derivatives for reducing secretion of stomach acid and therefore treating ulcers and gastritis.

Derwent Basic Abstract, Accession Number 83-724637, discloses synergistic anthelmintics containing 2-methylthio- or 2-methylsulphinyl-5-chloro-6,2,3-dichloro-phenoxy-benzimidazole with another benzimidazole.

Chemical Abstracts 71:49852j (1969) discloses 1,1,1-trichloro-5-(2-benzothiazolylthio)pentane; 1,1,1-trichloro-5(2-benzimidazolylthio)-pentane; 1,1,1-trichloro-5-(2-benzoxazolylthio)-pentane; 1,1-dichloro-3-(2-benzothiazolylthio)propene; 5-(2-benzothiazolylthio)pentanoic acid; 5-(2-benzoxazolylthio)pantanoic acid and 2-(2-benzothiazolylthio)ethanoic acid.

U.S. Pat. No. 3,792,170 discloses lower alkyl sulphinyl aryl aralkanoic acids which are useful as analgesics and antipyretics.

Derwent Basic Abstract, Accession Number 39933B, discloses antirheumatic, antiphlogistic zinc heterocyclic derivatives, e.g., zinc bis-(mercaptothiazole).

Derwent Basic Abstract, Accession Number 79347T, discloses isothiocyano-substituted benz(ox, thi or imid)azoles which are useful as anthelmintics. Derwent Basic Abstract, Accession Number 44280W, discloses biocidal 2-nitro-6-hetero-cyclythio-4-trifluoromethyl-benzonitriles such as the 6-(2-benzoxazolythio) compound.

Derwent Basic Abstract, Accession Number 66789T, discloses 5-nitro-2-thiazolyl sulphides and sulphones with antifungal activity.

Derwent Basic Abstract, Accession Number 01014X, discloses alpha-substituted-gamma-butyrolactone derivatives which have central nerve, antiinflammatory and antifungal activities.

Derwent Basic Abstract, Accession Number 66847Y, discloses (1,4)-disubstituted piperidine and piperazine derivatives for use as antiallergic agents.

Derwent Basic Abstract, Accession Number 52514D, discloses benzo-thiazolone derivatives having antiinflammatory, analgesic, antiallergic activities and also CNS-inhibitory activity.

Derwent Basic Abstract, Accession Number 29,132, discloses antimicrobial 2-phenyl-maleimides and succinimides.

Derwent Basic Abstract, Accession Number 32863R, discloses pyridylalkylthio- and pyridylalkyl-oxy-benzazoles which are useful as bacteriostats, anthelmintics and antiinflammatories.

INFORMATION DISCLOSURE

Derwent Basic Abstract, Accession Number 31650E, which abstracts Japanese patent application No. 57042607, discloses 2 mercapto-benzothiazole derivatives which are useful as herbicides.

U.S. Pat. No. 4,340,738 discloses a novel series of 2,3-dihydroimidazobenzothiazoles which display monoamine oxidase inhibiting activities and 2-aminobenzothiazole derivatives which are useful as intermediates thereto.

R. A. Glennon et al., J. Med. Chem. 24:766–69 (1981), discloses benz-fused mesoionic xanthine analogues which are useful as inhibitors of cyclic-AMP phosphodiesterase and certain 2-(Acylamino)- and 2-(Alkylamino) benzothiazoles which are useful as intermediates thereto.

P. T. S. Lau and T. E. Gompf, J. Org. Chem. 35:4103–08 (1970), discloses a variety of 2-amino-6-hydroxybenzothiazoles and N-substituted 2-amino-6-hydroxybenzothiazolyl compounds.

G. Foscolos and G. Tsatsas, Prakt. Akad. Athenon, 51:274–91 (1976), discloses the synthesis and pharmcodynamics of new benzothiazole derivatives and intermediates thereto.

Derwent Basic Abstract, Accession Number 06935U, discloses virustatic benzothiazole derivatives which are active against both DNA and RNA viruses.

Derwent Basic Abstract, Accession Number 13103B, which abstracts Japanese patent application 54003064, discloses benzothiazolyl thiocarboxylic acid derivatives with hypolipaemic action.

U.S. Pat. No. 3,985,762 discloses 2-alkylsulphinyl-6-nitrobenzothiazoles produced in high yield by nitration of 2-alkyl-mercaptobenzothiazoles with excess nitric acid in concentrated sulphuric acid, then oxidation.

U.S. Pat. No. 4,294,839 discloses 2-benzothiazol-2-yl-thio-2-arylalkanoic acid derivatives which are useful as hypolipaemic and antiarteriosclerotic agents.

Great Britain patent application 2100262A discloses pharmaceutical compositions with immuno-modulating activity containing 2-thio-2-arylpyrido- or -benzothiazole derivatives including new compounds.

Derwent Basic Abstract, Accession Number 73687E, discloses benzothiazole derivatives having immuno-regulating action, useful as antiallergic, anti-asthmatic, anti-rheumatic, carcinostatic and anti-rejection agents.

German patent application No. 3207640-A1 (Derwent Basic Abstract, Accession Number 83759615, discloses broncho-secretolytic and mucolytic preparations containing 2-allyl-thio-benzoxazole derivatives.

Derwent Basic Abstract, Accession Number 50123B, discloses herbicidal benzoxazole compounds which are non-toxic to soybeans and peanuts.

K. Tanaka et al., Chem. Pharm. Bull. 29:1876–86 (1981), discloses substituted thiazolo [3,2-a]benzimidazol-3(2H)-one and benzimidazole derivatives thereof.

French patent application 25,949 (Derwent Basic Abstract, Accession Number 27142), discloses thiazolylsulphinylbenzimidazoles and thiazolylthiobenzimidazoles and their use as parasiticides.

Derwent Basic Abstract, Accession Number 31315, discloses N-substituted benzylthiobenzimidazoles, which are antifungals, antibacterials, insecticides and acaricides.

Derwent Basic Abstracts, Accession Number 31326, discloses 2-(chlorobenzylmercapto)benzimidazole derivatives as bactericides, fungicides and anthelmintics.

Netherlands patent application No. 6803271 (Derwent Basic Abstract, Accession Number 33717), discloses mercapto-benzimidazoles as antiinflammatory, anti-pyretic and anti-depressive agents.

Derwent Basic Abstracts, Accession Numbers 23891V and 85200V, disclose N-substituted, 2-amino-2-thio-benzimidazoles prepared from corresponding thiols which are useful as anti-histaminics.

Derwent Basic Abstracts, Accession Numbers 78124T and 75480U, disclose 2-carboxyalkyl-3-hydroxy-3-phenyl-2,3-dihydro-thiazolo-(3,2-a)benzimidazoles and alkyl esters as CNS depressants and antituberculars.

H. O. Hankovszky and K. Hideg, Acta Chimica Academiae Scientiarum Hungaricae Tomus 53:405–16 (1967), discloses the preparation of 2-(N-arylideneamino)benzazoles and 2-(N-arylmethylamino)benzazoles and derivatives thereof.

O. Hankovszky et al., Hungary Pat. No. 156830, Dec. 22, 1969, relates to substituted benzazole derivatives.

European patent application No. 0001989 (Derwent Basic Abstract, Accession Number 40928B), discloses mercaptoalkanoamide derivatives which are useful as immunostimulants for auto-immune and immune deficient diseases.

U.S. Pat. Nos. 3,849,431 and 3,934,017 disclose isocyanato-benzoxazoles, benzothiazoles and benzimidazoles as anthelmintics and antimicrobials and aminointermediates thereto.

U.S. Pat. Nos. 4,216,160 and 4,329,363 and European patent application No. 0001989 disclose substituted mercapto acid amides which are useful as immunoregulants for correcting an imbalance of immune homeostasis.

Belgian patent application 754874 (Derwent Basic Abstract, Accession Number 13812S), discloses 2-chloromethylthiobenzazoles fungicide intermediates.

German patent application 2355092 (Derwent Basic Abstract, Accession Number 32702W), discloses fungicidal seed dressings containing substituted benzazole derivatives.

Derwent Basic Abstract, Accession Number 13611R, discloses 2-(thiocyanomethyl sulphonyl and sulphinyl)-benzothiazoles, benzoxazoles and benzimidazoles, which are active against microorganisms in agricultural and industrial processes.

Derwent Basic Abstract, Accession Number 00373W, discloses antifouling marine paints using thiocyantobenzoxazole, -thiazole or -imidazole derivatives.

European patent application No. 0006347 (Derwent Basic Abstract, Accession Number 02065C), discloses the regulation of the growth of leguminous plants by the application of benz-heterocyclyl-thio-alkanoic acid or its ester, salt, amide or nitrile.

German patent application No. 2913527 (Derwent Basic Abstract, Accession Number 75476C), discloses synergistic insecticide and acaricide compositions containing benzoxazole or benzothiazole compounds and another pesticide, e.g., a carbamate, pyrethroid, organophosphorus or haloalkane compound.

Derwent Basic Abstract, Accession Number 10360, discloses 2-aralkylmercapto-benzazoles which are used as therapeutics.

Derwent Basic Abstract, Accession Number 36066, discloses 2[dialkylamino (or piperidino) ethylthio]-benzoxazoles, optionally substituted, as local anaesthetics.

SUMMARY OF THE INVENTION

The present invention particularly provides:
A compound of formula I

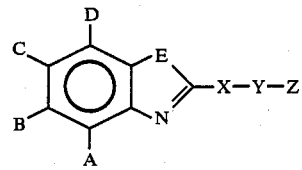

wherein A is:
(1) H, or
(2) OH;
wherein B is:
(1) H,
(2) OH, or
(3) OCH$_3$;
wherein C is:
(1) H,
(2) OH,
(3) tetrahydropyran-2-yl-oxy, or
(4) NHCO(CH$_2$)$_2$COOH;
wherein D is:
(1) H,
(2) OH, or
(3) OCH$_3$;
wherein E is:
(1) O,
(2) S, or
(3) NH;
wherein X is:
(1) O,
(2) S, or
(3) NH;
wherein Y is (CH$_2$)$_n$;
wherein Z is:
(1) (C$_3$-C$_6$) cycloalkyl,
(2) exo or endo 2-norbornyl,
(3) 1-adamantyl,
(4) t-butyl,
(5) 3-cyclohexenyl,
(6) 2-cyclohexanolyl,
(7) 2-cyclohexanone,
(8) H,
(9) Cl,
(10) Br,
(11) CN,
(12) OCOCH$_3$,
(13) COOCH$_3$,
(14) C≡CH,
(15) CH=CH$_2$,

(16) CH=CH(C1-C4)alkyl,
(17) CH=CH-phenyl,
(18) CH(Br)CH₃,
(19) CH(CH₃)phenyl,
(20) CH(CH₃)p-tolyl,
(21) phenyl unsubstituted or substituted at the 4 position with one of the following:
  (a) bromine, or
  (b) COOCH₃;
(22) benzoyl,
(23) toluyl,
(24) 2-naphthyl,
(25) 9-anthracenyl,
(26) 2-tetrahydrofuranyl,
(27) phthalimido,
(28) 2-benzimidazolyl,
(29) 2-mcercapto-6-hydroxybenzothiazolyl, or
(30) 7-methoxy-coumarin-4-yl; and pharmaceutically acceptable salts thereof; wherein n is 4–11, except when Z is:
  (a) exo or endo 2-norbornyl,
  (b) 1-adamantyl,
  (c) t-butyl,
  (d) 3-cyclohexenyl,
  (e) 2-cyclohexanolyl, or
  (f) 2-cyclohexanone; then n is 0;
and with the proviso that A, B, C and D are not all hydrogen.

A compound selected from the group consisting of:
2-[[3-(Diethylamino)propyl]amino]-6-benzothiazolol;
2-[[3-(Diethylamino)propyl]amino]-6-benzothiazolol, hydroquinone dihydrochloride salt;
2-[[3-(Diethylamino)propyl]amino]-6-benzothiazolol dihydrochloride.

The carbon atom content of various hydrocarbon-containing moieties is indicated by a prefix designating the minimum and maximum number of carbon atoms in the moiety, i.e., the prefix (Ci-Cj) indicates a moiety of the integer "i" to the integer "j" carbon atoms, inclusive. Thus (C1-C3)alkyl refers to alkyl of one to 3 carbon atoms, inclusive, or methyl, ethyl, propyl, and isopropyl.

Examples of alkyl of one to 10 carbon atoms, inclusive, are methyl, ethyl, propyl, butyl, pentyl, hexyl, heptyl, octyl, nonyl, decyl, and isomeric forms thereof.

Examples of C2-C10 alkenyl are allyl, 1-methylallyl, 2-methylallyl (methallyl), 2-butenyl (crotyl), 3-butenyl, 1,2-dimethylallyl, 1,1-dimethylallyl, 2-ethyllalyl, 1-methyl-2-butenyl, 2-methyl-2-butenyl, 3-methyl-2-butenyl, 3-pentenyl, 2,3-dimethyl-2-butenyl, 1,1,2-trimethylallyl, 1,3-dimethyl-2-butenyl, 1-ethyl-2-butenyl, 4-methyl-2-pentenyl, 2-ethyl-2-pentenyl, 4,4-dimethyl-2-pentenyl, 2-heptenyl, 2-octenyl, 5-octenyl, 1,4-dimethyl-1-hexenyl, and the like.

Examples of acids, which are commonly used for salt formation, are hydrochloric acid, hydrobromic acid, hydroiodic acid, methanesulfonic acid, ethanesulfonic acid, benzenesulfonic acid, phosphoric acid, acetic acid, propionic acid, succinic acid, para-toluenesulfonic acid, maleic acid, tartaric acid, and lactic acid.

The compounds of the present invention will be named herein using the Chemical Abstracts numbering system (see Naming and Indexing of Chemical Substances for Chemical Abstracts during the Ninth Collective Period (1972-1976), a reprint of section IV from the Volume 76 Index Guide.) When E is sulfur, the compounds are named as benzothiazoles. When E is oxygen, the compounds are named as benzoxazoles, and when E is NH, the compounds are named as benzimidazoles.

As noted, compounds of this invention are useful to inhibit the formation of slow reacting substance of anaphylaxis (SRS-A) and thus its smooth muscle contracting and secretory effects.

Several of the compounds of the present invention were also tested for their inhibitory effect on mucus secretion in the canine tracheal secretion model. The most active benzothiazole 6-[(6-hydroxy-2-benzothiazolyl)amino]hexanoic acid methyl ester caused marked inhibition on all three end points, producing 21.8%, 63.4%, and 100% inhibition on baseline, hypoxia, and Indomethacin blocked/Arachidonic Acid (AA) induced mucus secretion, respectively. Other compounds that caused inhibition were: 2-(5-hexenylthio)-H-benzimidazol-6-ol, 2-(5-hexenylthio)-6-benzothiazolol maleic acid salt, and 2-[[3-(diethylamino)propyl]amino]-6-benzothiazolol, hydroquinone dihydrochloride salt, 2-[[3-(diethylamino)propyl]amino]-6-benzothiazolol, 2-[[3-(diethylamino)propyl]amino]-6-benzothiazolol dihydrochloride and 6-[[6-[(3-carboxy-1-oxopropyl)amino]-2-benzothiazolyl]thio]hexanoic acid methyl ester, tromethamine salt. Also the known compound 2-(2-propenylamino)-6-benzothiazolol caused inhibition of mucus secretion when tested in the canine model.

To demonstrate the SRS-A inhibitory activity of the compounds of this invention, compounds of this invention were evaluated in a standard laboratory test. This test is conducted in rat mononuclear cells incubated in the presence of cysteine and challenged with a calcium ionophore (which induces SRS-A formation).

Some ot the compounds of the present invention were also tested for lipoxygenase inhibition. Arachidonic acid is added to washed human platelets and the oxygen uptake is measured using oxygraph cells. A decrease of oxygen uptake versus the control cell indicates inhibition of lipoxygenase. For a full description of the procedure see, Wallach, et al., Biochim, Biophys. Acta. 231:445 (1976).

The known compound 2-(2-propenylamino)-6-benzothiazolol was found to be active in the inhibition of both the leukotriene and lipoxygenase systems.

Some of the novel compounds of this invention have been shown to be active as inhibitors of the production of leukotrienes. Some of the compounds of this invention have been shown to be active as inhibitors of the lipoxygenase enzyme system. Some of the compound of this invention have been shown to be active as mucus inhibitors in mammals. Some of these compounds are effective in all three systems. All of the compounds of this invention are active as inhibitors of at least one of these three systems. Accordingly, these novel compounds are useful for administration to mammals, including humans, whenever it is desirable medically to inhibit one of these systems. Inhibitors of these systems are useful in the treatment of asthma.

Thus, all of the compounds of this invention are useful in the treatment of asthma. For example, these compounds are useful as bronchodilators or as inhibitors of mediators such as SRS-A which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations, by inhalation in the form of aerosols or solutions from nebulizers; or by insufflation in the form of powder. Doses in the range of about 0.01 to 50 mg per kg of body weight are used 1 to 4 times a day, the exact dose depending on the age, weight, and condition of the patient and on the frequency and route of administration. For the above use these compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

As noted above, the compounds of this invention are particularly useful in treating asthma, but any allergy wherein slow reacting substance of anaphylaxis (SRSA) is thought to be involved as a pharmacological mediator of anaphylaxis can be treated. For example, the compounds can be used for treatment of such conditions as allergic rhinitis, food allergy and urticaria as well as asthma.

The compounds of this invention are effectively administered to human asthma patients by any convenient route such as oral inhalation, aerosol inhalation, parenterally, (orally, intravenously, interperitoneally), transdermally, topically and the like.

For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bissulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

The lipoxygenase inhibitor compounds of this invention are useful whenever it is desired to inhibit platelet aggregation, reduce the adhesive character of platelets, and remove or prevent the formation of thrombi in mammals, including man, rabbits, dogs, and rats. For example, these compounds are useful in the prevention of myocardial infarcts, to prevent post-operative thrombosis, to promote patency of vascular grafts following surgery, and to treat conditions such as atherosclerosis, arteriosclerosis, blood clotting defects due to lipemia, and other clinical conditions. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These lipoxygenase inhibitor compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

Hammerstroöm, et al. Science 197: 994–996 (1977) notes the role of 12-lipoxygenase in psoriasis. Doig, et al., Prostaglandins 20: 1007–1019 (1980) and Lin, et al., J. Clin. Invest. 70: 1058 (1982) disclose that 5-lipoxygenase inhibitors block platelet thrombus formation. Dawson, et al., in SRS-A and Leukotrienes, 219–226 (Wiley and Sons 1981) note that 5-lipoxygenase inhibitors block neutrophil "recruitment" during inflammatory diseasessuch as arthritis.

In addition, 5-lipoxygenase inhibitors prevent the production of slow-reacting substance of anaphylaxis (SRS-A), now known to be a mixture of leukotrienes. (Leukotrienes are synthesized using 5-lipoxygenase.) SRS-A mediates the symptoms and pathophyisology of asthma. See Murphy, et al., Proc. Nat. Acad. Sci. USA, 4275–4279 (1979). Thus, the 5-lipoxygenase inhibitors disclosed herein are useful in the treatment of asthma.

5-Lipoxygenase products have been implicated in essential hypertension (Chand, et al., Microcirculation 1: 111–123 (1981), and gout (Rae, et al., Lancet 1122–1124 (Nov. 20, 1982), indicating that the 5-lipoxygenase inhibitors disclosed herein are useful in treating these conditions as well. Further, neutrophil depletion, such as that induced by 5-lipoxygenase inhibitors, has been shown to cause a significant decrease in infarct size following circumflex artery occlusion. See Romson, et al., Circulation 66: 85 (1982). Thus, the 5-lipoxygenase inhibitors herein may be useful in the protection of the myocardium following infarct.

The lipoxygenase inhibitors of the present invention are also useful for the prevention or treatment of deep vein thrombosis (DVT). This method comprises the administration of a compound of the [Formula I] to a mammal susceptible to DVT.

By "deep vein thrombosis" (DVT) is meant the thrombosis (clot formation) of the lower limb deep veins (deeply situated veins). Such thrombosis is frequently a result of major surgery, massive trauma, myocardial infarction, neoplasia, and pregnancy. The term "deep vein thrombosis" or "DVT" is meant to encompass the thrombosis resulting from these or any other causes.

By "prevention" in this context is meant the total or partial avoidance of clot formation in the deep veins of a mammal.

The present invention includes the treatment of each of various mammalian species, including humans. With respect to non-humans, the present invention is particularly and especially concerned with treating domesticated animals, for example, cattle, dogs, cats and swine. Humans are the most preferred mammals to be treated by the methods of this invention.

Any convenient route of administration is employed. Thus, oral formulation and oral administration is, for example, the preferred route for use in humans although parenteral (e.g., intravenous, intraperitoneal, and intramuscular) administration is also employed.

The dosage regimen for the lipoxygenase inhibitor compounds used to treat deep vein thrombosis will depend on a variety of factors, including the type, age, weight, sex, and medical condition of the mammal, and most importantly on the risks and probable consequences of deep vein thrombosis. It is within the skill of the attending physician or veterinarian to determine the risks of deep vein thrombosis, and to prescribe an effective amount of the lipoxygenase inhibitors claimed herein. Equivalent dosages for other routes of administration are also employed. Similarly, when other lipoxygenase inhibitors are employed, equipotent doses are administered based on the compound's comparative potency as determined in standard laboratory tests.

The most preferred use of these compounds is as SRS-A inhibitors, e.g., in the treatment of asthma.

The compounds of the present invention are prepared by the methods depicted in Charts A, B, C and D. The variables are as defined above. $R_1$ is defined as chlorine, bromine, or other good-leaving group.

Chart A depicts the preparation of substituted 2-mercaptobenzothiazoles, benzoxazoles and benzimidazoles, wherein E is sulfur, oxygen or amino, respectively. In Chart A, some 2-mercaptobenzothiazoles of formula A-1, which are used as starting materials, are commercially available. The 2-mercaptobenzothiazole compounds of formula A-1 which are not commercially available can be readily prepared by those skilled in the art using procedures known in the art and starting materials available in the art. For example, 6-hydroxy-2-mercaptobenzothiazole may be prepared by dealkylation of the 6-ethoxy-2-mercaptobenzothiazole, which is commercially available with aluminum chloride. Also, 6-fluoro-2-mercaptobenzothiazole can conveniently be prepared from p-fluoroaniline. Reaction of p-fluoroaniline with thiocyanogen gives the 6-fluoro-2-aminobenzothiazole compound. The 6-fluoro-2-aminobenzothiazole compound can be hydrolyzed with 50% potassium hydroxide and then recyclized with carbon disulfide to give 6-fluoro-2-mercaptobenzothiazole. In a similar manner, the 4-methoxy-2-aminobenzothiazole may be prepared and converted to 4-methoxy-2-mercaptobenzothiazole, which is then demethylated with aluminum chloride to produce the 4-hydroxy-2-mercaptobenzothiazole.

Some 2-mercaptobenzimidazoles and benzoxazoles of formula A-1, which are used as starting materials in Chart A, are commercially available. The 2-mercaptobenzimidazole and benzoxazole compounds of formula A-1 which are not commercially available can be readily prepared by those skilled in the art. For example, 6-hydroxy-2-mercaptobenzimidazole is prepared via reaction of 4-methoxy-o-phenylene diamine with carbon disulfide in potassium hydroxide to give the known methoxybenzimidazole, which can be dealkylated with aluminum chloride to afford the 6-hydroxy derivative. 6-hydroxy-2-mercaptobenzoxazole is prepared by the reaction of 4-aminoresorcinol and thiophosgene.

According to the procedure of Chart A, the 2-mercapto compound of formula A-1 is reacted in a basic solution, e.g., dimethylformamide/triethylamine; dimethylsulfoxide/triethylamine; or 1N sodium hydroxide/tetrahydrofuran; with the appropriate 6-bromo derivative of formula A-2 to produce the [2-substituted]-2-mercapto compound of formula A-3.

Chart B depicts the preparation of substituted 2-aminobenzothiazoles, benzimidazoles and benzoxazoles. Some 2-chloro compounds of formula B-1, which are used as starting materials in Chart B, are commercially available. The 2-chloro compounds of formula B-1 which are not commercially available can readily be prepared by methods known in the art. For example, diazotization of 6-methoxy-2-aminobenzothiazole, which is commercially available, followed by treatment with cuprous chloride gives 6-methoxy-2-chlorobenzothiazole. The methyl group is easily removed by aluminum chloride to give 6-hydroxy-2-chlorobenzothiazole. This compound can in turn be acylated to produce 6-acetoxy-2-chlorobenzothiazole or treated with dihydropyran to produce the 6-tetrahydropyran-2-chloro derivative.

According to the procedure of Chart B, the substituted 2-amino compounds of formula B-3 are synthesized via displacement of the 2-chloro substituent of the 2-chloro compounds of formula B-1, wherein hydroxy substituents are protected, with the appropriate amine of formula B-2.

Chart C depicts an alternative method by which the 6-hydroxy 2-aminobenzothiazoles are prepared. The starting materials for Chart C are commercially available or can be prepared by methods known in the art. In Chart C, 6-hydroxy-2-amino compounds of formula C-3 are prepared via the [hydrochloric acid]-catalysed reaction of thioureas of formula C-2 with 1,4-benzoquinones of formula C-1. Occasionally, the product of this reaction is not readily isolated but can be separated by chromatography on silica gel. Also, the product may hang onto the solvent of recrystallization making absolute purification difficult.

Chart D depicts the preparation of substituted 2-oxybenzothiazoles, benzoxazoles and benzimidazoles. The 2-chloro compounds of formula D-1, which are used as starting materials in Chart D, are prepared as described above for Chart B. In Chart D, the 2-chloro compound of formula D-1 is reacted with the appropriate alkoxide derivative of formula D-2 (from sodium hydride) in tetrahydrofuran to produce the 2-oxy compound of formula D-3.

Certain compounds of the present invention are preferred. Thus, compounds of the Formula II are the most preferred compounds of this invention.

A compound according to claim 1 of formula II

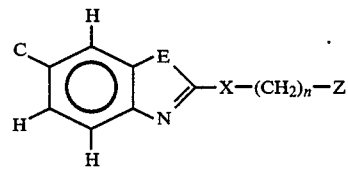

wherein C is:
(1) OH, or (2) NHCO(CH$_2$)$_2$COOH;
wherein E is:
  (1) S, or
  (2) NH;
wherein X is:
  (1) S, or
  (2) NH;
wherein n is 4–11;
wherein Z is:
  (1) H,
  (2) CH=CH$_2$, or
  (3) COOCH$_3$;
and pharmaceutically acceptable salts thereof.

DESCRIPTION OF THE PREFERRED EMBODIMENTS

The present invention is seen more fully by the Examples given below.

The following abbreviations are used in the preparations and examples below:

Skellysolve B (SSB); dimethyl sulfoxide (DMSO); thin layer chromatography (TLC); nuclear magnetic resonance spectra (NMR); mass spectra (mass spec); infrared spectra (infra red); tetrahydrofuran (THF); medium pressure liquid chromatography (MPLC column); Karl Fisher (KF).

Preparation 1

6-Hydroxy-2-mercaptobenzothiazole (Formula A-1: A, B and D are H; C is OH; E is S)

6-Ethoxy-2-mercaptobenzothiazole (16.88 g) is suspended in 800 ml of toluene and aluminum chloride (42.72 g) is added. The mixture is heated at reflux for 3 hours during which a green solution results. After cooling, 200 ml of 2N hydrochloric acid is added dropwise at which time a pinkish solid precipitates. After cooling, the precipitate is suction filtered overnight. This solid, for the most part, dissolves in 180 ml of 1N sodium hydroxide to produce a very dark solution. The solution is stirred with Darco and filtered through a Celite pad to leave a yellow-green solution. This solution is diluted with one-third the volume of 95% ethanol. Glacial acetic acid (12 ml) is added and a white solid precipitates. The mixture is cooled, suction filtered, and washed with diethylether to afford 12.29 g, mp 283°–7° C. after drying, of the title compound.

Physical characteristics are as follows:
Analysis Found: C, 44.64; H, 2.79; N, 7.59; S, 33.43.
Mass Spec (m/e): 185, 184, 183, 182, 155, 154, 151, 150, 125, 119.
Infra Red (cm$^{-1}$, Nujol): 3252, 3199, 1589, 1504, 1425, 1345, 1211, 1030, 913, 865.

Preparation 2

6-Fluoro-2-mercaptobenzothiazole (Formula A-1: A, B and D are H; C is F; E is S)

p-Fluoroaniline (11.1 g) is added to acetic acid (75 ml) and cooled in an ice bath. Ammonium thiocyanate (29 g) is added followed by a solution of bromine (6 ml, 18.7 g) in acetic acid (25 ml) over 15 min. Stirring is continued for an additional 1 hr. Then the reaction is heated on a steam bath for 15 min. After cooling, water (400 ml) is added to the orange suspension. The reaction is cooled in an ice-methanol bath and carefully neutralized with concentrated ammonia, keeping the internal temperature below 30° C. The yellow solid is filtered and washed with water (200 ml). The solid is stirred in acetone (250 ml) and a small amount of amorphous solid filtered. Evaporation gives a yellow solid. Recrystallization from chloroform-hexane (containing a little acetone), with a Darco treatment gives the 2-amino derivative as pale yellow crystals, mp 181°–183° C.

The 2-amino derivative (8.4 g) is heated under reflux in 50% potassium hydroxide solution (50 ml) for 1.25 hr. The solution is cooled and carbon disulfide (5.7 g) are added. The mixture is gently refluxed for 2 hrs during which it acquires a red color. On cooling, a pinkish solid is filtered which is dissolved in water (300 ml) and cooled in an ice-ethanol bath. Careful addition of acetic acid causes a yellow solid to separate and copious gas evolution. The solid is filtered, dried, and recrystallized from chloroform-acetone-hexane, with a Darco treatment, to give yellow crystals, mp 224°–225.5° C. (3.91 g) of the title compound.

Physical characteristics are as follows:
Analysis Found: C, 45.21; H, 2.40; N, 7.53; S, 35.40.
Mass Spec (m/e); 187, 186, 185, 153, 127, 126, 121, 114, 92.
Infra Red (cm$^{-1}$, $\nu_{max}$): 1862, 1588, 1497, 1473, 1328, 1197, 1037, 911, 852, 805, 702, 664.

Preparation 3

2-Mercapto-4-methoxybenzothiazole (Formula A-1: B, C and D are H; A is OCH$_3$; E is S)

2-Amino-4-mehoxybenzothiazole (18.0 g) and 45% potassium hydroxide (100 ml) are heated under reflux for 4 hr. Upon cooling, carbon disulfide (9.0 ml, 11.4 g) is added followed by water (50 ml). The mixture is gently refluxed for 2 hr, then poured into water (500 ml). After cooling in an ice-methanol bath, it is carefully neutralized with acetic acid, when gas evolution occurs. The yellow precipitate is filtered and chromatographed over silica gel (500 g). Elution with dichloromethane gives the product which is recrystallized from acetone as shiny white plates, mp. 204°–206° C. (5.75 g) of the title compound.

Physical characteristics are as follows:
Analysis Found: C, 48.37; H, 3.61; N, 7.22; S, 32.74.
Mass Spec (m/e): 199, 198, 197, 196, 182, 179, 168, 167, 154.
Infra Red (cm$^{-1}$, $\nu_{max}$): 1616, 1608, 1589, 1581, 1494, 1466, 1457, 1446, 1424, 1284, 1241, 1201, 1160, 1069, 1033, 758, 677.
UV ($\lambda$, ethanol): 210, 225, 245, 254, 264, 219.

Preparation 4

4-Hydroxy-2-mercaptobemnzothiazole (Formula A-1: A is OH; B, C an D are H; E is S)

2-Mercapto-4-methoxybenzothiazole (4.0 g) is stirred in toluene (200 ml) and aluminum chloride (10.8 g) added. The stirred mixture is heated under reflux for 3 hr then allowed to cool, and 1N hydrochloric acid (100 ml) added. The solids are filtered and mostly dissolved in 1N sodium hydroxide (50 ml). After filtration through a bed of celite, the solution is acidified with acetic acid. The gray solid is filtered and recrystallized from methanol, with a Darco treatment, to give white needles, mp 253.5°–255.5° C. (2.7 g) of the title compound.

Physical characteristics are as follows:
Analysis Found: C, 45.56; H, 2.82; N, 7.80; S, 35.17.
Mass Spec (m/e): 185, 184, 183; 182, 107, 96, 91, 79.

Infra Red (cm$^{-1}$, $\nu_{max}$): 3347, 3129, 3083, 3053, 1629, 1617, 1585, 1292, 1250, 1240, 1165, 1154, 1067, 914, 767, 753, 739, 717, 680.

UV ($\lambda$, ethanol): 210, 225, 240, 255, 267, 319.

NMR ($\delta$, D$_6$DMSO): 6.70–7.00; 7.00–7.30; 11.83.

Preparation 5

2-Mercapto-6-methoxybenzimidazole (Formula A-1: A, B and D are H; C is OCH$_3$; E is NH0

A mixture of 4-methoxy-o-phenylenediamine hydrochloride (10.0 g), potassium hydroxide (6.8 g), carbon disulfide (4 ml), ethanol (60 ml) and water (10 ml) are heated under reflux for 2.5 hr. After cooling slightly, Darco (3 g) is added and the reaction heated under reflux for an additional 10 min. The Darco is filtered off through celite and the filtrate warmed on a steam bath to 70° C. Hot water (60 ml) is added followed by acetic acid (5 ml) and water (10 ml). On cooling in an ice bath an orange solid separates. The solid is filtered, washed with water, and dried to provide the title product, mp 261°–263° C. (6.75 g).

Preparation 6

6-Hydroxy-2-mercaptobenzimidazole (Formula A-1: A, B and D are H; C is OH; E is NH)

2-Mercapto-6-methoxybenzimidazole (5.0 gI( is suspended in toluene (250 ml) and aluminum chloride (14.8 g) added. The mixture is stirred and heated to reflux for 3 hr, then cooled and 1N hydrochloric acid (125 ml) added. The precipitate is filtered and washed with water then dissolved in 1N sodium hydroxide (75 ml). A small amount of insoluble material is filtered and the filtrate treated with acetic acid. A brown solid is filtered (3.9 g) and recrystallized from acetone-Skellysolve B as rose colored prisms, mp 287°–290° C. (3.65 g) of the title compound.

Physical characteristics are as follows:

Analysis Found: C, 50.58; H, 3.74; N, 16.72; S, 18.64.

Mass Spec (m/e): 167, 166, 165, 138, 137, 134, 83, 80.

Infra Red (cm$^{-1}$, $\nu_{max}$): 3224, 3131, 1702, 1641, 1629, 1524, 1512, 1498, 1280, 1229, 1223, 1204, 1159, 1144, 1125, 1115, 979, 962, 864, 836, 798, 791, 779, 757, 739, 671, 667, 636, 618.

UV ($\lambda$, ethanol): 209, 215, 221, 253, 312, 318.

Preparation 7

6-Hydroxy-2-mercaptobenzoxazole (Formula A-1: A, B and D are H; C is OH; E is O)

4-Aminoresorcinol hydrochloride (4.845 g) is dissolved in 20% potassium hydroxide (75 ml) and thiosphosgene (3.9 g) added dropwise with stirring. After 3 hr the mixture is cooled in ice and acetic acid added. The resultant dark brown precipitate is collected and chromatographed over silica gel (300 g). Elution with 2.5% methanol-dichloromethane gives the title product (2.42 g) which is recrystallized from acetone-Skellysolve B as a greenish tan solid, mp 295°–296.5° C. (1.99 g).

Preparation 8

2-Chloro-6-methoxybenzothiazole (Formula B-1 (D-1): A, B and D are H; C is OCH$_3$; E is S)

2-Amino-6-methoxybenzothiazole (36.0 g) is dissolved in a mixture of formic acid (100 ml), acetic acid (40 ml) and concentrated hydrochloric acid (80 ml), then cooled to −5° C. A solution of sodium nitrite (14.0 g) in water (20 ml) is added dropwise with stirring and then stirred an additional 15 minutes at 0° C. Cuprous chloride (44.0 g) in concentrated hydrochloric acid (150 ml) is then added to the vigorously stirred mixture and then allowed to warm to room temperature over 30 minutes. The reaction is heated to 60° C. on a steam bath then allowed to cool. The brown solid is filtered and washed well with water. After drying it is extracted with three 250 ml portions of boiling dichloromethane and the combined extracts chromatographed over silica gel (750 g) eluting with dichloromethane. The product is rapidly eluted and obtained as a pale yellow oil which crystallizes on cooling. Recrystallization from Skellysolve B, with a Darco treatment, gives pale yellow needles, mp 53°–54.5° C. (22.25 g) of the title compound.

Physical characteristics are as follows:

Analysis Found: C, 48.12; H, 3.06; N, 7.16; S, 15.76, Cl, 17.85.

Mass Spec (m/e): 201, 200, 199, 186, 184, 158, 156, 95, 69.

Infra Red (cm$^{-1}$, $\nu_{max}$): 1601, 1558, 1267, 1254, 1225, 1211, 1191, 1183, 1076, 1024, 1012, 893, 838, 812.

UV ($\lambda$, ethanol): 208, 217, 222, 243, 276, 298.

NMR ($\delta$, CDCl$_3$): 3.20, 6.94, 7.07, 7.70.

Preparation 9

2-Chloro-6-benzothiazolol (Formula B-1 (D-1): A, B and D are H; C is OH; E is S)

2-Chloro-6-methoxybenzothiazole (5.0 g) is dissolved in toluene (175 ml) and anhydrous aluminum chloride (9.35 g) added. The mixture is heated to reflux for 1 hour, then allowed to cool. 1N hydrochloric acid (175 ml) is added and the resultant precipitate filtered. The solid is washed with water (100 ml) then stirred with saturated sodium bicarbonate. The solid is filtered again and washed with water. Recrystallization from acetone—Skellysolve B gives pale yellow prisms, mp 174°–6° C. (4.43 g) of the title compound.

Physical characteristics are as follows:

Analysis Found: C, 45.38; H, 2.27; N, 7.72; S, 16.98; Cl, 19.49.

Mass Spec (m/e): 187, 186, 185, 124, 122, 96, 94, 70, 69.

Infra Red (cm$^{-1}$, $\nu_{max}$): 3147, 3070, 1605, 1490, 1267, 1229, 1070, 1022, 911, 831, 808, 734, 712, 690.

UV ($\lambda$, ethanol): 209, 217, 223, 244, 279, 289, 299.

NMR ($\delta$, D$_6$ acetone): 7.04, 7.37, 7.72, 8.95.

Preparation 10

2-Chloro-6-benzothiazolol acetate (ester) (Formula B-1 (D-1): A, B and D are H; C is OCOCH$_3$; E is S)

2-Chloro-6-benzothiazolol (1.0 g) is dissolved in a mixture of acetonitrile (5 ml) and acetic anhydride (5 ml) then stirred for 1 hour. The solvent is removed in vacuo and the clear residue taken up in dichloromethane (25 ml) and washed with water (50 ml). After drying over sodium sulfate, filtering and evaporating the resultant solid is recrystallized from acetone—Skellysolve B as tan needles, mp 106°–8° C. (1.17 g) of the title compound.

Physical characteristics are as follows:

Analysis Found: C, 47.40; H, 2.66; N, 6.38; S, 13.94; Cl, 15.71.

Mass Spec (m/e): 229, 227, 188, 187, 186, 185, 96, 95.

Infra Red (cm$^{-1}$, $\nu_{max}$): 3102, 1769, 1665, 1565, 1487, 1481, 1450, 1315, 1239, 1225, 1206, 1192, 1186, 1126, 1025, 1016, 938, 891, 826, 818, 602.

UV ($\lambda$, ethanol): 216, 236, 259, 282, 294.

NMR ($\delta$, CDCl$_3$): 2.36, 7.18, 7.53, 7.90.

Preparation 11

2-Chloro-6[(tetrahydro-2H-pyran-2-yl)oxy]benzothiazole (Formula B-1) (D-1): A, B and D are H; C is tetrahydropyranyloxy; E is S)

2-Chloro-6-benzothiazolol (4.5 g) is dissolved in methylene chloride saturated with pyridinium hydrochloride. Dihydropyran (12 ml) is added and the solution heated on a steam bath for 2 hours then 2 days at room temperature. The solvent is removed to leave a syrup, which is dissolved in dichloromethane (50 ml) and washed with two 50 ml portions of water, dried with sodium sulfate, then chromatographed over silica gel (200 g). The product is eluted with dichloromethane as a syrup which slowly crystallizes (4.2 g). Recrystallization from Skellysolve B gives white crystals, mp 65°–67° C. of the title compound.

Physical characteristics are as follows:

Analysis Found: C, 53.01; H, 4.48; N, 5.38; S, 13.58; Cl, 12.26.

Mass Spec (m/e): 269, 188, 187, 186, 185, 85, 84, 67.

Infra Red (cm$^{-1}$, $\nu_{max}$): 1606, 1559, 1353, 1344, 1287, 1283, 1247, 1219, 1204, 1181, 1247, 1219, 1204, 1181, 1126, 1113, 1049, 1042, 1022, 1011, 974, 931, 895, 882, 872, 865, 819, 810, 619, 601.

UV ($\lambda$, ethanol): 290, 217, 243, 273, 278, 297.

NMR ($\delta$, CDCl$_3$): 1.0–2.35; 3.35–4.10; 5.39; 7.12; 7.42; 7.78.

EXAMPLE 1

6-Benzothiazolol-2-(3-butenylthio)- (Formula A-3: A, B and D are H; C is OH; E is S; Y is (CH$_2$)$_n$; n is 2; Z is CH=CH$_2$) (Refer to Chart A)

6-Hydroxy-2-mercaptobenzothiazole (1 g) is dissolved in 11 ml of 1N sodium hydroxide. 4-Bromo-1-butene (0.824 g) dissolved in 5 ml of tetrahydrofuran is added. The solution is stirred at room temperature. TLC (10% methanol/trichloromethane) indicates some reaction after 1 hour but much greater conversion after stirring overnight. Acetic acid (1 ml) is added and the tetrahydrofuran removed on the rotary evaporator. The aqueous mixture is extracted with ethyl acetate, dried over magnesium sulfate and concentrated. The resulting oil is dissolved in methanol/trichloromethane and absorbed on to 20 g of silica gel (230–400 mesh). An MPLC solumn is run eluting with 15% ethyl acetate/SSB to leave ;B 830 mg, mp 89.5°–91° C. of the title compound after recrystallization from trichloromethane/hexane.

Physical characteristics are as follows:

Analysis Found: C, 55.41; H, 4.74; N, 5.81; S, 26.32.

Mass Spec (m/e): 237, 204, 185, 183, 196, 184, 152, 55, 45, 39.

Infra Red (cm$^{-1}$, Nujol): 3154, 2903, 2870, 1642, 1599, 1466, 1451, 1221, 1011, 908.

NMR ($\delta$, D$_6$-acetone): 2.5, 3.35, 5.2, 6.85, 6.95, 7.3, 76.

EXAMPLE 2

6-Benzothiazolol,2-(2-butenylthio)- (Formula A-3: A, B and D are H; C is OH; E is S; Y is (CH$_2$)$_n$; n is 1; Z is CH=CH—CH$_3$) (Refer to Chart A)

6-Hydroxy-2-mercaptobenzothiazole (1 g) is dissolved in 5 ml of N,N-dimethylformamide (DMF) and triethylamine (1.1 g) is added. Crotyl bromide (891 mg) is added and the solution stirred overnight at room temperature. TLC (10% methanol/trichloromethane) indicates good conversion to a faster moving spot. The DMF is removed on the vacuum pump, and the residue dissolved in ethyl acetate and washed with water. The ethyl acetate is dried over magnesium sulfate and filtered. This material is absorbed onto 20 g of silica gel (230–400 mesh) and an MPLC column is run eluting with 10% methanol/trichloromethane. Concentration leaves a light yellow solid. Recrystallization from trichloromethane/SSB gives 820 mg, mp 142°–9;20 C., of the title compound.

Physical characteristics are as follows:

Analysis Found: C, 55.37; H, 4.66; N, 5.96; S, 26.53.

Mass Spec (m/e): 237, 222, 208, 204, 184, 183, 182, 138, 55, 39.

Infra Red (cm$^{-1}$, Nujol): 2954, 2855, 1607, 1563, 1458, 1429, 1346, 1285, 1230, 1022.

NMR ($\delta$, d$_6$-acetone): 1.6, 4.85, 6.7, 6.9, 7.3, 7.6.

EXAMPLE 3

6-Benzothiazolol,2-(Cyclopentylthio) (Formula A-3: A, B and D are H; C is OH; E is S; Y is (CH$_2$)$_n$; n is 0; Z is cyclopentyl) (Refer to Chart A)

6-Hydroxy-2-mercaptobenzothiazole (2 g) is dissolved in 10 ml of N,N-dimethylformamide (DMF) and triethylamine (2.2 g) is added. Cyclopentylbromide (4 g) is added and the solution stirred at room temperature overnight. TLC (10% methanol/trichloromethane) indicates good conversion to a faster moving spot. The DMF is removed on the vacuum pump and water added to the residue. The aqueous mixture is extracted with ethyl acetate, dried over magnesium sulfate and concentrated. The residue is purified on an MPLC column eluting with 25% ethyl acetate/SSB. The resulting solid is recrystallized from trichloromethane/SSB to leave 1.8 g, mp 147°–148.5° C., of the title compound.

Physical characteristics are as follows:

Analysis Found: C, 55.62; H, 5.06; N, 5.41; S, 24.57.

Mass Spec (m/e): 252, 251, 218, 185, 184, 183, 182, 154, 41, 39.

Infra Red (cm$^{-1}$, Nujol): 2932, 2857, 1599, 1468, 1447, 1377, 1225, 1120, 1024, 909.

NMR ($\delta$, d$_6$-acetone): 1.7, 4.0, 6.88, 7.2, 7.55.

EXAMPLES 2–24

The compounds of Table I below were prepared in accordance with the procedure of Examples 1, 2 or 3 above, but substituting the haloderivative indicated. All of the compounds of Table I are of formula A-3 wherein A, B and D are H; C is OH; E is S; Y is (CH$_2$)$_n$; and the other variables are as defined.

TABLE I

| Eg. No. | Halo-Derivative | n | Z | MP (°C.) |
|---|---|---|---|---|
| 4 | 5-bromo-1-pentene | 3 | CH=CH$_2$ | 103.5–105 |

TABLE I-continued

| Eg. No. | Halo-Derivative | n | Z | MP (°C.) |
|---|---|---|---|---|
| 5 | 6-bromo-1-hexene | 4 | CH=CH$_2$ | 74–75 |
| 6 | 5-chloro-1-pentyne | 3 | C≡CH | 91–92.5 |
| 7 | 3-bromocyclohexene | 0 | 2-cyclohexenyl | 150–152.5 |
| 8 | n-hexylbromide | 6 | H | 94–96 |
| 9 | cyclopropylmethylbromide | 1 | cyclopropyl | 145–148 |
| 10 | benzylbromide | 1 | phenyl | 155–157 |
| 11 | 2-bromoethylbenzene | 2 | phenyl | 127–128.5 |
| 12 | 1-bromo-3-phenylpropane | 3 | phenyl | 135.5–138 |
| 13 | p-bromobenzylbromide | 1 | 4-bromophenyl | 188–191 |
| 14 | α-bromo-p-toluic acid-methyl ester | 1 | benzoic acid-methyl ester | 138–140 |
| 15 | cinnamyl bromide | 1 | 3-phenyl-ethylenyl | 172–174.5 |
| 16 | (2-bromomethyl)-naphthalene | 1 | 2-naphthyl | 174–176 |
| 17 | 9-(chloromethyl)-anthracene | 1 | 2-anthracenyl | 201–203.5 |
| 18 | 2-chloromethyl-benzimidazole | 1 | 2-benzimidazolyl | 242–244 |
| 19 | 1-chloro-6-hydroxyhexane | 6 | OH | 84.5–86.5 |
| 20 | 5-bromopentylacetate | 5 | OCOCH$_3$ | 79–80.5 |
| 21 | 6-bromocapronitrile | 5 | CN | 79–81 |
| 22 | 2-chlorocyclohexanone | 0 | 2-oxocyclohexyl | 94–98 |
| 23 | 1,6-dichlorohexane | 6 | Cl | 109.5–111 |
| 24 | 1,6-dibromohexane | 6 | Br | 107–109 |

EXAMPLE 25

2-[6-[(6-Hydroxy-2-benzothiazolyl)thio]hexyl]-1H-Isoindole-1,3(2H)-dione (Formula A-3: A, B and D are H; C is OH; E is S; Y is (CH$_2$)$_n$; n is 6; Z is isoindole-1,3(2H)-dione) (Refer to Chart A).

Triethylamine (2.21 g) is added to a mixture of 6-hydroxy-2-mercaptobenzothiazole (2.0 g) and N-(6-bromohexyl)phthalimide (3.39 g) in N,N-dimethylformamide (DMF) (25 ml) and the mixture stirred at room temperature for 18 hours. The mixture is warmed briefly to 95° C. and then cooled and the precipitate, triethylamine hydrochloride, filtered and discarded. The filtrate is poured over ice (400 g) and stirred for 2 hours at room temperature and the resultant precipitate filtered, washed with water (200 ml) and dried (4.1 g). Chromatography over silicon dioxide (300 g) eluting with 1.5% methanol/dichloromethane gives a pale yellow solide that is crystallized from acetone giving pale yellow prisms (3.1 g), mp 164°–165.5° C., of the title compound.

Physical characteristics are as follows:
Analysis Found: C, 60.94; H, 4.87; N, 6.75; S, 15.66.
Mass Spec (m/e): 413, 412, 365, 252, 197, 184, 183, 160, 139.
Infra Red (cm$^{-1}$, ν$_{max}$): 3403, 1775, 1696, 1595, 1403, 1224, 1049, 1006, 843, 719.
UV (λ max): 221, 224, 242, 251, 294, 299, 309.
NMR (δ, d$_6$-DMSO): 1.00, 3.23, 3.54, 6.87, 7.24, 7.69, 7.78, 9.66.

EXAMPLE 26

Benzothiazol-6-ol,[(1,3-propandiyl)bis(thio)] (Formula A-3: A, B and D are H; C is OH; E is S; Y is (CH$_2$)$_n$; n is 3; Z is 6-hydroxy-2-mercaptobenzothiazolyl) (Refer to Chart A).

6-Hydroxy-2-mercaptobenzothiazole (2 g) is dissolved in 10 ml of N,N-dimethylformamide (DMF) and triethylamine (2.2 g) is added. 1,3-Dibromopropane (2.67 g) is added and the solution stirred at room temperature overnight. TLC (10% methanol/trichloromethane) indicates conversion to a faster moving material. The DMF is removed on the vacuum pump and water is added to the residue. The aqueous mixture is extracted with ethyl acetate, dried over magnesium sulfate, and concentrated. The residue is purified on an MPLC column eluting with 35% ethyl acetate/SSB to leave 300 mg, mp 196°–198.5° C., of the title compound as a white solid after recrystallization from ethyl acetate/SSB.

Physical characteristics are as follows:
Analysis Found: C, 50.40; H, 3.69; N, 6.62; S, 30.64.
Mass Spec (m/e): 406, 225, 224, 223, 208, 190, 183, 182, 178, 152.
Infra Red (cm$^{-1}$, Nujol): 3237, 1603, 1456, 1427, 1377, 1222, 1018, 813.
NMR (δ, d$_6$-DMSO): 2.2, 3.5, 6.8, 7.2, 7.55.

EXAMPLE 27

6-Benzothiazolol,2-(Cyclohexylthio)- (Formula A-3: A, B and D are H; C is OH, E is S; Y is (CH$_2$)$_n$; n is 0; Z is cyclohexyl) (Refer to Chart A).

6-Hydroxy-2-mercaptobenzothiazole (1 g) is dissolved in 10 ml of DMSO and triethylamine (1.11 g) is added. Cyclohexylbromide (994 mg) is added and the solution stirred overnight at room temperature. TLC (10% methanol/trichloromethane) indicates very little conversion to product. Heating at 60° C. affects good conversion to a faster moving spot. The DMSO solution is poured into water and extracted with trichloromethane. The trichloromethane is washed with water, dried over magnesium sulfate and concentrated. The resulting oil is dissolved in trichloromethane and applied to a gravity silica gel column eluting with 25% ethyl acetate/SSB to leave a white solid (1 g). Recrystallization from methanol/water leaves 550 mg, mp 154°–6° C., of the title compound.

Physical characteristics are as follows:
Analysis Found: C, 58.81; H, 5.71; N, 5.16; S, 24.24.
Mass Spec (m/e): 267, 266, 265, 232, 185, 184, 183, 182, 55, 41.
Infra Red (cm$^{-1}$, Nujol): 2946, 2931, 1599, 1467, 1446, 1225, 1025, 909, 836, 813.
NMR (δ, polysol-d): 1.4–2.1, 3.7, 6.8, 7.3, 7.7.

EXAMPLE 28

6-Benzothiazolol,2-(bicyclo[2.2.1]hept-2-ylthio)(Formula A-3 A, B and D are H; C is OH; E is S; Y is $(CH_2)_n$; n is 0; Z is exo-2-norbornyl) (Refer to Chart A).

6-Hydroxy-2-mercaptobenzothiazole (1 g) is dissolved in 10 ml of DMSO and triethylamine (1.11 g) is added. exo-2-Bromonorbornane (1.07 g) is added and the solution heated at 60° C. for 2 hr. TLC (10% methanol/trichloromethane) indicates good conversion to a faster moving spot. The DMSO is partially removed on the vacuum pump, dissolved in 10% methanol/trichloromethane and absorbed onto silica gel (230-400 mesh). An MPLC column is run eluting with 15% ethyl acetate/SSB and 287 mg of a white solid is obtained. This material is recrystallized from toluene to leave 280 mg, mp 195°-6° C., of the title compound.

Physical characteristics are as follows:
Analysis Found: C, 60.66; H, 5.36; N, 5.03; S, 22.79.
Mass Spec (m/e): 277, 210, 197, 185, 184, 183, 178, 95, 67, 41.
Infra Red (cm$^{-1}$, Njuol): 3176, 2957, 2927, 1602, 1478, 1430, 1376, 1227, 1020, 842.
NMR ($\delta$, polysol-d): 0.9-2.2, 3.9, 6.7, 7.2, 7.6.

EXAMPLE 29

Hexanoic Acid, 6-[[6-hydroxy-2-benzothiazolyl]thio]methyl ester (Formula A-3: A, B and D are H; C is OH; E is S; Y is $(CH_2)_n$; n is 5; Z is COOCH$_3$) (Refer to Chart A).

A mixture of 1.99 g of 2-mercapto-6-hydroxybenzothiazole, 3.06 g of the methyl orthoester of 6-bromohexanoic acid and 1.38 g of potassium carbonate in 50 ml of acetone are stirred for 40 hr. The mixture is then poured into 200 ml of 5% hydrochloric acid.

The resultant crystals are filtered and dissolved in methylene chloride. The organic phase is washed with water, dried over sodium sulfate and concentrated. The product is recrystallized from ethyl acetate to yield 2.05 g of the title compound, mp 97.5°-99° C.

Physical characteristics are as follows:
Analysis Found: C, 53.96; H, 5.47; N, 4.67.

EXAMPLE 30

2-(5-Hexenylthio)-4-benzothiazolol (Formula A-3: A is OH; B, C and D are H; E is S; Y is $(CH_2)_n$; n is 4; Z is CH=CH$_2$) (Refer to Chart A).

4-Hydroxy-2-mercaptobenzothiazole (0.5 g) is dissolved in 1N sodium hydroxide (2.73 ml) and stirred overnight with 6-bromo-1-hexene (0.54 g) in tetrahydrofuran (5 ml). The reaction is then refluxed for 30 min, cooled and the tetrahydrofuran removed in vacuo. The aqueous solution is treated with acetic acid (0.3 ml); water (10 ml) is added and the mixture extracted with two 50 ml portions of trichloromethane. The combined trichloromethane extracts are washed with two 50 ml portions of water, dried with sodium sulfate, filtered and evaporated to yield an amber oil. The oil is chromatographed over a column of silicon dioxide (75 g) made up in Skellysolve B. Gradient elution up to 20% dichloromethane-Skellysolve B gives the title product. Recrystallization from Skellysolve B gives long fine white needles, mp 49°-51.5° C. (0.64 g).

Physical characteristics are as follows:
Analysis Found: C, 58.73; H, 5.54; N, 5.22; S, 24.42.
Mass Spec (m/e): 265, 232, 218, 204, 184, 183, 178, 107.
Infra Red (cm$^{-1}$, $\nu_{max}$): 3384, 3313, 1894, 1826, 1807, 1641, 1575, 1286, 1268, 1233, 1225, 1172, 1158, 1058, 1028, 1020, 996, 921, 911, 770, 765, 732.
UV ($\lambda$, ethanol): 206, 227, 248, 280, 286, 310.
NMR ($\delta$, CDCl$_3$): 1.20-2.30, 3.27, 4.85-5.20, 5.50-6.05, 6.80-7.35.

EXAMPLE 31

6-Fluoro-2-(hexylthio)benzothiazole (Formula A-3: A, B and D are H; C is F; E is S; Y is $(CH_2)_n$; n is 6; Z is H) (Refer to Chart A).

6-Fluoro-2-mercaptobenzothiazole (1.85 g) is dissolved in 1N sodium hydroxide (10 ml) and treated with 1-bromohexane (1.65 g) in tetrahydrofuran (10 ml). After stirring overnight, acetic acid (1 ml) is added and the tetrahydrofuran removed on a rotary evaporator. The aqueous residue is extracted with two 50 ml portions of trichloromethane, washed with water (50 ml), dried with sodium sulfate, filtered and evaporated. The resultant oil is chromatographed over silicon dioxide eluting with dichloromethane. The title product is obtained as a clear oil which would only crystallize at ice temperatures (2.17 g).

Physical characteristics are as follows:
Analysis Found: C, 58.39; H, 6.17; N, 5.26; S, 25.14, F, 7.22.
Mass Spec (m/e): 269, 222, 199, 186, 185, 73, 61.
Infra Red (cm$^{-1}$, $\nu_{max}$ (Neat)): 1601, 1569, 1471, 1449, 1405, 1254, 1195 998, 909, 846, 811.
UV ($\lambda$, Ethanol): 227, 244, 281, 290, 302.
NMR ($\delta$, CDCl$_3$): 1.60-2.05, 3.30, 7.09, 7.37, 7.75.

EXAMPLE 32

2-[(5,6,7-Trimethoxy-2-benzothiazolyl)thio]cyclohexanol (Formula A-3: A is H; B, C and D are OCH$_3$; E is S; Y is $(CH_2)_n$; n is 0; Z is 2-cyclohexanolyl) (Refer to Chart A).

2-Mercapto-5,6,7-trimethoxybenzothiazole (0.80 g) is suspended in acetonitrile (20 ml) and cyclohexene oxide (0.485 g) and triethylamine (0.345 g) added. The reaction is heated to reflux for 3 hr, then the solvent removed in vacuo to afford an oil. The oil is chromatographed over a column of silicon dioxide (100 g) made up in dichloromethane. Elution with dichloromethane followed by 0.25% methanol/dichloromethane gives the title product as a pale amber syrup (0.92 g).

Physical characteristics are as follows:
Analysis Found: C, 53.26; H, 5.83; N, 3.85; S, 17.38.
Mass Spec (m/e): 357, 356, 355, 271, 259, 258, 257, 243, 242, 199.
Infra Red (cm$^{-1}$, $\nu_{max}$): 3386, 1598, 1562, 1299, 1235, 1198, 1164, 1113, 1074, 1028, 1005, 988, 960, 853, 845, 821, 729.
UV ($\lambda$, Ethanol): 209, 230, 250, 290, 304, 311.
NMR ($\delta$, CDCl$_3$): 1.10-1.90, 2.00-2.40, 3.45-3.70, 3.85, 3.87, 4.00, 4.60, 7.12.

EXAMPLE 33

6-Benzothiazolol,2-[(2-hydroxycyclohexyl)thio] (Formula A-3: A, B and D are H; C is OH; E is S; Y is $(CH_2)_n$; n is 0; Z is 2-cyclohexanolyl) (Refer to Chart A).

6-Hydroxy-2-mercaptobenzothiazole (1 g) is dissolved in DMSO (10 ml) and triethylamine (1.11 g) is added. Cyclohexene oxide (600 mg) is added and the solution stirred at room temperature for 2 hrs. with no apparent reaction by TLC (25% ethyl acetate/SSB). After heating at 60° C. for 1 hr., TLC (50% ethyl acetate/SSB) indicates a faster moving spot. The DMSO solution is added to water and extracted with diethylether. The diethylether is dried over magnesium sulfate and concentrated. The residue is redissolved in 10% methanol/trichloromethane and absorbed onto silica gel. A gravity column is run eluting with 50% ethyl acetate/SSB. The resulting oil crystallizes when triturated with SSB. Recrystallization from diethylether/SSB leaves 600 mg, mp 120°-121° C., of the title compound.

Physical characteristics are as follows:
Analysis Found: C, 55.75; H, 5.52; N, 4.91; S, 22.43.
Mass Spec (m/e): 281, 197, 185, 184, 183, 167, 114, 81, 80, 79.
Infra Red (cm$^{-1}$, Nujol): 3203, 3153, 2811, 1600, 1468, 1443, 1265, 1234, 1067, 1007.
NMR ($\delta$, d$_6$-acetone): 1.25–2.5, 3.05, 3.65, 7.0, 7.35, 7.7.

EXAMPLE 34

4-[[2-(5-Hexenylthio)-6-benzothiazolyl]amino]-4-oxobutanoic acid (Formula A-3: A, B and D are H; C is 4-amino-4-oxobutanoic acid; E is S; Y is (CH$_2$)$_n$; n is 4; Z is CH=CH$_2$).

2-(5-hexenylthio)-6-amino-benzothiazole (2.0 g) and succinic anhydride (0.8 g) are heated under reflux in acetonitrile for 2 hr. The product which separates on cooling (2.52 g) is filtered and recrystallized from acetonitrile giving white plates, mp 144°-145.5° C. (2.2 g) of the title compound.

Physical characteristics are as follows:
Anaylsis Found: C, 56.31; H, 5.57; N, 7.62; S, 17.78.
Mass Spec (m/e): 364, 264, 217, 203, 183, 182, 181, 177, 137.
Infra Red (cm$^{-1}$, $\nu_{max}$): 3291, 1694, 1653, 1577, 1526, 1282, 1214, 1190, 1008, 990, 985, 913, 849, 826, 738, 734, 731, 651.
UV ($\lambda$, Ethanol): 224, 243, 296, 301, 313.
NMR ($\delta$, D$_6$DMSO): 1.25–2.30, 2.63, 3.32, 4.80–5.20, 5.55–6.05, 7.52, 7.78, 8.38, 10.17, 12.00.

EXAMPLE 35

4-[[2-(5-hexenylthio)-6-benzothiazolyl]amino]-4-oxobutanoic acid tromethamine salt (Formula A-3: A, B and D are H; C is 4-amino-4-oxobutanoic acid tromethamine salt; E is S; Y is (CH$_2$)$_n$; n is 4; Z is CH=CH$_2$)

4-[[2-(5-Hexenylthio)-6-benzothiazolyl]amino]-4-oxobutanoic acid (1.0 g) and tromethamine (THAM) (0.458 g) are stirred for 3 hr in methanol (20 ml) then the solvent removed in vacuo. The resultant clear oil slowly crystallizes and is recrystallized from methanol (1.1 g). A second recrystallization from acetone gives fine white needles, mp 105° C. (sinters), 155° C. (melts and bubbles), (1.04 g) of the title compound.

Physical characteristics are as follows:
Analysis Found: C, 51.73; H, 6.44; N, 8.51; S, 13.46.
Mass Spec (m/e): 264, 182, 181, 137, 90, 72, 60.
Infra Red (cm$^{-1}$, $\nu_{max}$): 3393, 3291, 3262, 1666, 1639, 1623, 1611, 1583, 1538, 1300, 1282, 1260, 1242, 1229, 1207, 1180, 1174, 1082, 1047, 1038, 1021, 1008, 963, 897, 819, 734, 721, 716, 649.
UV ($\lambda$, Ethanol): 224, 239, 301, 312.

EXAMPLE 36

6-[[6-(Acetyloxy)-2-benzothiazolyl]thio]hexanoic acid methyl ester (Formula A-3: A, B and D and H; C is OCOCH$_3$; E is S; Y is (CH$_2$)$_n$; n is 5; Z is COOCH$_3$)

6-[[6-(Hydroxy)-2-benzothiazolyl]thio]hexanoic acid methyl ester (0.25 g) is dissolved in a mixture of acetic anhydride (5 ml) and pyridine (5 ml) containing a few crystals of 4-dimethylaminopyridine and stirred at room temperature for 3 hrs. Removal of the solvent leaves a clear oil which is dissolved in trichloromethane (5 ml), washed with water (20 ml) and dried over sodium sulfate. The solvent is removed leaving a clear oil which crystallizes from ether-Skellysolve B at 0° C. giving white needles, mp 43.5°-45° C. (0.24 g) of the title compound.

Physical characteristics are as follows:
Analysis Found: C, 54.23; H, 5.37; N, 3.90; S, 18.45.
Mass Spec (m/e): 353, 322, 311, 264, 197, 184, 183, 182, 69, 43.
Infra Red (cm$^{-1}$, $\nu_{max}$): 1748, 1736, 1596, 1568, 1208, 1219, 1187, 1176, 1165, 1143, 1115, 1017, 999, 928, 893, 848, 827, 660, 601.
UV ($\lambda$, Ethanol): 225, 244, 283, 290, 302.
NMR ($\delta$, CDCl$_3$): 1.30–2.05, 2.33, 2.35, 3.32, 3.65, 7.12, 7.47, 7.79.

EXAMPLE 37

6-[(7-Bromo-6-hydroxy-2-benzothiazolyl)thio]hexanoic acid methyl ester (Formula A-3: A and B are H; C is OH; D is Br; E is S; Y is (CH$_2$)$_n$; n is 5; Z is COOCH$_3$).

To a suspension of the 6-[6-hydroxy-2-benzothiazolyl)thio]hexanoic acid methyl ester (0.5 g) in carbon tetrachloride (15 ml) is added bromine (0.259 g) in carbon tetrachloride (1 ml) with stirring at room temperature over a period of 1 hr. TLC indicates about 25-30% unreacted starting material is still present and additional bromine solution (0.2 ml) is added dropwise. TLC indicates about the same degree of reaction as before the additional bromine is added. Trichloromethane (75 ml) is added. The solution is washed with two 50 ml portions of 5% sodium bicarbonate and water (50 ml) and dried over sodium sulfate. Removal of the solvent leaves an amber oil. Chromatography on silicon dioxide and elution with 1% methanol/dichloromethane fails to separate the product and starting material. The fractions containing the mixture are combined and rechromatographed on silicon dioxide eluting with 1.5 liters of 0.25% methanol/dichloromethane. 150 ml fractions are collected. Fractions 2-4 contain the pure title product and are combined and crystallized from carbon tetrachloride giving pale yellow prisms, mp 98°-99.5° C. (0.37 g).

Physical characteristics are as follows:
Anaylsis Found: C, 42.90; H, 4.05; N, 3.55; S, 16.24; Br, 21.52.
Mass Spec (m/e): 391, 389, 344, 263, 261, 69, 59, 55, 41, 15.
Infra Red (cm$^{-1}$, $\nu_{max}$): 3336, 1706, 1606, 1551, 1299, 1279, 1269, 1220, 1197, 1185, 1005, 936, 878, 809, 668, 661, 608.
UV ($\lambda$, Ethanol): 210, 226, 230, 244, 250, 292, 298, 310.
NMR ($\delta$, CDCl$_3$): 1.20–2.05, 2.33, 3.27, 3.68, 7.06, 7.06, 7.64.

EXAMPLE 38

6-[(4-Hydroxy-2-benzothiazolyl)thio]hexanoic acid methyl ester (Formula A-3: A is OH; B, C and D are H; E is S; Y is $(CH_2)_n$; n is 5; Z is $COOCH_3$).

6-[(4,Hydroxy-2-benzothiazolyl)thio]hexanoic acid (0.80 g) is dissolved in a 20:1 mixture (30 ml) of methanol/thionyl chloride and stirred for 3 hr. The solvent is removed to afford a tan solid which is stirred in a mixture of chloroform (30 ml) and saturated sodium bicarbonate (30 ml). The organic layer is washed with water (50 ml), dried with sodium sulfate, filtered and evaporated. The resulting solid is recrystallized from methanol, with a Darco treatment, to give fine white needles, mp 63°–64.5° C. (0.70 g) of the title compound.

Physical characteristics are as follows:

Analysis Found: C, 53.73; H, 5.47; N, 4.49; S, 20.51.

Mass Spec (m/e): 311, 264, 197, 184, 183, 107, 69.

Infra Red (cm$^{-1}$, $\nu_{max}$): 3415, 1728, 1576, 1271, 1260, 1227, 1219, 1200, 1172, 1161, 1147, 1043, 923, 774, 742, 731.

UV ($\delta$, Ethanol): 206, 226, 248, 280, 286, 310.

NMR ($\delta$, $CDCl_3$): 1.80–2.00, 2.30, 3.26, 3.65, 6.80–7.35.

EXAMPLE 39

2-(5-Hexenylthio)-1H-benzimidazol-6-ol (Formula A-3: A, B and D are H; C is OH; E is NH; Y is $(CH_2)_n$; n is 4; Z is $CH=CH_2$) (Refer to Chart A).

6-Hydroxy-2-mercaptobenzimidazole (1.0 g) is dissolved in 1N sodium hydroxide (6 ml) and 6-bromo-1-hexane (0.98 g) added in tetrahydrofuran (6 ml). The mixture is stirred overnight then the tetrahydrofuran removed in vacuo. The residue is treated with two 250 ml portions of ethyl acetate and the organic extracts washed with water (25 ml). After drying with sodium sulfate, filtering and evaporating, an oil is obtained that is chromatographed over silcon dioxide (100 g). Elution with dichloromethane followed by 3% methanol/dichloromethane affords the title product which is recrystallized from acetone-dichloromethane as white crystals, mp 115°–117° C. (0.35 g).

Physical characteristics are as follows:

Analysis Found: C, 62.68; H, 6.69; N, 11.07; S, 12.53.

Mass Spec (m/e): 248, 233, 215, 201, 187, 167, 166, 165, 138.

Infra Red (cm$^{-1}$, $\nu_{max}$): 3201, 3132, 2600, 1865, 1632, 1606, 1293, 1257, 1224, 1208, 1165, 1118, 999, 956, 908, 838, 813, 712, 629.

UV ($\lambda$, Ethanol): 207, 249, 299.

NMR ($\delta$, $D_6$-acetone): 1.20–2.25, 3.27, 4.70–5.15, 5.40–6.00, 6.73, 6.95, 7.32.

EXAMPLE 40

2-(5-Hexenylthio)-6-benzoxazolol (Formula A-3: A, B and D are H; C is OH; E is O, Y is $(CH_2)_n$; n is 4; Z is $CH=CH_2$) (Refer to Chart A).

6-Hydroxy-2-mercaptobenzoxazole (1.0 g) is dissolved in 1N sodium hydroxide (6.0 ml) and 6-bromo-1-hexene (1.075 g) is added in tetrahydrofuran (6 ml). After stirring overnight, the solvent is removed and the aqueous residue extracted with three 25 ml portions of trichloromethane. The combined extracts are washed with water (50 ml), dried with sodium sulfate, filtered and evaporated to give a dark oil. The oil is chromatographed over silicon dioxide (75 g) eluting with dichloromethane. There is obtained an amber oil (900 mg) which crystallizes upon cooling. Recrystallization from Skellysolve B gives the title compound as white prisms, mp 45°–57° C. (620 mg).

Physical characteristics are as follows:

Anaylsis Found: C, 62.83; H, 6.07; N, 5.64; S, 12.91.

Mass Spec (m/e): 249, 216, 202, 188, 168, 167, 138.

Infra Red (cm$^{-1}$, $\nu_{max}$): 3067, 1642, 1632, 1605, 1507, 1486, 1283, 1269, 1228, 1211, 1131, 1096, 957, 910, 847, 833, 628.

UV ($\lambda$, Ethanol): 256, 294.

NMR ($\delta$, $CDCl_3$): 1.10–2.20, 3.24, 4.70–5.10, 5.40–5.95, 6.78, 6.97, 7.33.

EXAMPLE 41

N-5-Hexenyl-6-[(tetrahydro-2H-pyran-2-yl)oxy]-2-benzothiazolamine (Formula B-3: A, B and D are H; C is tetrahydropyran-2-yloxy; E is S; Y is $(CH_2)_n$; n is 4; Z is $CH=CH_2$) (Refer to Chart B).

The 6-tetrahydropyran derivative of 2-chloro-6-hydroxybenzothiazole (3.54 g) and 5-hexenylamine (4.43 g) are heated under reflux overnight in acetonitrile (10 ml). The solvent is removed and the residue dissolved in dichloromethane (25 ml) and washed with saturated sodium bicarbonate (25 ml). After drying with sodium sulfate and removing the solvent, the residue is chromatographed over silixon dioxide (200 g). Elution with dichloromethane followed by 0.5% methanol/dichloromethane gives the product as a clear glass which slowly crystallizes (4.11 g). Recrystallization from Skellysolve B gives an off-white solid, mp 66°–68° C. (3.68 g) as the title compound.

Physical characteristics are as follows:

Analysis Found: C, 64.70; H, 7.08; N, 8.50; S, 9.65.

Mass Spec (m/e): 332, 249, 248, 180, 179, 166, 152, 98, 85.

Infra Red (cm$^{-1}$, $\nu_{max}$): 3213, 3108, 3074, 1639, 1617, 1562, 1264, 1219, 1207, 1181, 1125, 1112, 1043, 984, 966, 935, 909, 900, 873, 846, 811.

UV ($\lambda$, Ethanol): 226, 271, 305, 313.

NMR ($\delta$, $CDCl_3$): 1.15–2.25, 3.34, 3.45–4.15, ˙4.80–5.15, 5.30, 5.45–6.00, 6.14, 6.95, 7.28, 7.35.

EXAMPLE 42

2-(Cyclohexylamino)-6-benzothiazolol (Formula C-3: A, B and D are H; Y is $(CH_2)_n$; n is 0; Z is cyclohexyl) (Refer to Chart C).

1,4-Benzoquinone (2.16 g) is dissolved in hot ethanol (40 ml) and added dropwise to a stirred solution of cyclohexylthiourea (1.58 g) in ethanol (20 ml) and concentrated hydrochloric acid (0.9 ml). The mixture is stirred for 18 hours at room temperature and then heated briefly to reflux and the solvent removed in vacuo. The residue is stirred in water (50 ml) and a borwn solid collected by filtration and washed with two 25 ml portions of water. The filtrate is neutralized with 5% sodium bicarbonate and a brown precipitate collected by filtration and washed with water and dried. This solid is chromatographed over silicon dioxide in a medium pressure column eluting with trichloromethane at 20 psi and 17 ml/min. The unreacted 1,4-benzoquinone is eluted as the first component and then the product is eluted with 2% methanol/trichloromethane and crystallized from trichloromethane as white prisms, (1.15 g), mp 109°–111° C., still containing trichloromethane. Recrystallizing from methanol/water gives white prisms (0.75 g), mp 147° C., of the title compound.

Physical characteristics are as follows:
Analysis Found: C, 60.49; H, 6.66; N, 10.78; S, 13.01.
K.F. Found: Water, 3.37%.
Mass Spec (m/e): 248, 167, 166, 165, 139, 85, 83, 55, 41, 28.
Infra Red (cm$^{-1}$, $\nu_{max}$): 3307, 2605, 1615, 1581, 1553, 1526, 1277, 1271, 1251, 1217, 1082, 863, 842, 761.
UV ($\lambda_{max}$): 224, 272, 305, 312.
NMR ($\delta$, D$_6$Acetone): 1.00–1.90, 1.90–2.40, 3.55, 3.50–4.00, 6.73, 7.06, 7.24.

EXAMPLES 43–47

The compounds of Table II below were prepared in accordance with the procedure of Example 42 above, but substituting the thiourea derivative indicated. All of the compounds of Table II are of formula C-3, wherein A, B and D are H; Y is (CH$_2$)$_n$; and the other variables are as defined.

| Eg. No. | Thiourea Derivative | n | Z | MP (°C.) |
|---|---|---|---|---|
| 43 | tert-butylthiourea | 0 | tert-butyl | 130 |
| 44 | 1-adamantylthiourea | 0 | 1-adamantyl | 112–114 |
| 45 | 1-benzyl-2-thiourea | 1 | phenyl | 179.5–181.5 |
| 46 | 1-(3-phenylpropyl)-2-thiourea | 3 | phenyl | 155–157 |
| 47 | 1-(2-tetrahydrofurfuryl)-2-thiourea | 1 | 2-furanyl | 199–200.5 |

EXAMPLE 48

Endo-2-(Bicyclo[2.2.1]hept-2-ylamino)-6-benzothiazolol and 7-Chloro derivative (Formula C-3: A and B are H; D is H or Cl; Y is (CH$_2$)$_n$; n is 0; Z is endo-2-norbornyl) (Refer to Chart C).

1,4-Benzoquinone (3.81 g) is dissolved in ethanol (75 ml) and added dropwise to a stirred solution of 1-(endo-2-norbornyl)-2-thiourea (3.0 g) in ethanol (35 ml) and concentrated hydrochloric acid (1.6 ml). The mixture is stirred for 18 hours at room temperature during which time a white solid precipitates and is filtered, washed twice with 20 ml portions of acetonitrile and dried. The filtrate is taken to dryness and the residue combined with the filtered solid. The combined materials are treated with sodium bicarbonate solution and extracted with chloroform. After drying and filtering the chloroform is evaporated. The residue is chromatographed over silicon dioxide in a medium pressure column eluting with 1% methanol/trichloromethane at 20 psi and 17 ml/min. The first component eluted is the 6-hydroxy-7 chloro derivative of the title compound that is crystallized from trichloromethane giving white prisms (0.65 g), mp 184.5°–186° C.

Physical characteristics are as follows:
Analysis Found: C, 56.81; H, 5.07; N, 9.41; S, 10.79; Cl, 12.77.
Mass Spec (m/e): 296, 295, 294, 227, 202, 201, 200, 95.
Infra Red (cm$^{-1}$, $\nu_{max}$): 3365, 3350, 1608, 1569, 1547, 1509, 1279, 1260, 1253, 1223, 1203, 899, 809, 605.
UV ($\lambda_{max}$): 228, 270, 307, 316.
NMR ($\delta$, D$_6$-DMSO): 0.65–1.75, 1.75–2.30, 3.75–4.20, 6.84, 7.14, 7.88, 9.72.

The second component eluted from the column is the 6-hydroxy derivative of the title compound that is crystallized from acetone giving white prisms (1.62 g), mp 211°–213° C.

Physical characteristics are as follows:
Analysis Found: C, 64.62; H, 6.29; N, 10.80; S, 12.53.
Mass Spec (m/e): 261, 260, 193, 191, 178, 167, 166, 165, 95.
Infra Red (cm$^{-1}$, $\nu_{max}$): 3270, 1610, 1585, 1563, 1284, 1240, 1221, 1206, 1177, 1169, 862, 840, 811, 620.
UV ($\lambda_{max}$): 224, 273, 305, 315.
NMR ($\delta$, D$_6$-DMSO): 0.70–1.80, 1.80–2.35, 3.80–4.20, 6.64, 7.03, 7.16, 7.67, 9.04.

EXAMPLE 49

Exo-2-(Bicyclo[2.2.1]hept-2-ylamino)-7-chloro-6-benzothiazolol (Formula C-3: A and B are H; D is Cl; Y is (CH$_2$)$_n$; n is 0; Z is exo-2-norbornyl) (Refer to Chart C).

1,4-Benzoquinone (6.34 g) is dissolved in hot ethanol (90 ml) and added dropwise to a stirred suspension of 1-(exo-2-norbornyl)-2-thiourea (5.0 g) in ethanol (50 ml) and concentrated hydrochloric acid (2.6 ml). The mixture is stirred for 18 hours at room temperature during which time a tan solid precipitates. This solid is filtered and washed with acetonitrile (25 ml) and ethanol (10 ml) and dissolved in water (10–15 ml) and neutralized with 5% sodium bicarbonate. The resultant tan solid is filtered and washed with water and dried and recrystallized twice from acetone (Darco) giving white prisms (1.33 g), mp 193°–195° C., of the title compound.

Physical characteristics are as follows:
Analysis Found: C, 57.36; H, 5.59; N, 9.12; S, 10.10; Cl, 10.79.
Mass Spec (m/e): 296, 295, 294, 227, 202, 201, 200, 95, 67, 41.
Infra Red (cm$^{-1}$, $\nu_{max}$): 3363, 3286, 2574, 2491, 1708, 1610, 1604, 1592, 1550, 1533, 1520, 1286, 1274, 1243, 1223, 1208, 1173, 1114, 895, 884, 818, 801.
UV ($\lambda_{max}$): 228, 274, 307, 314.
NMR ($\delta$, D$_6$-DMSO): 0.90–1.95, 2.15–2.40, 3.56, 6.85, 7.17, 7.74, 9.74.

EXAMPLE 50

2-(2-Propenylamino)-6-benzothiazolol (Formula C-3: A, B and D are H; Y is (CH$_2$)$_n$; n is 1; Z is CH=CH$_2$).

6-Methoxy-2-propenylamino-benzothiazole (1.0 g) and aluminum chloride (1.82 g) are heated under reflux in toluene (40 ml) for 6 hr then allowed to cool. 1N hydrochloric acid (20 ml) is added and the mixture stirred for 30 min. The toluene is removed in vacuo and the aqueous residue adjusted to pH 7–8 with saturated sodium bicarbonate then extracted with three 25 ml portions of trichloromethane. The trichloromethane extracts are washed with saturated sodium bicarbonate (25 ml), water (100 ml), dried with sodium sulfate, filtered and evaporated to afford a light brown semisolid. Chromatography over silicon dioxide (75 g) eluting with 1% methanol/trichloromethane gives a clear glass which crystallizes upon trituration with trichloromethane. Recrystallization from acetone-Skellysolve B gives white prisms of the title compound, mp 129°–131° C., (0.65 g).

Physical characteristics are as follows:
Analysis Found: C, 58.07; H, 4.93; N, 13.51; S, 15.46.
Mass Spec (m/e): 207, 206, 205, 191, 179, 178, 166, 165, 121.
Infra Red (cm$^{-1}$, $\nu_{max}$): 3329, 3086, 1649, 1612, 1585, 1564, 1448, 1416, 1366, 1333, 1308, 1285, 1218, 1106, 1052, 995, 972, 945, 860, 844, 812, 640.
UV ($\lambda$, Ethanol): 223, 270, 303, 311.
NMR ($\delta$, D$_6$-Acetone): 4.05, 4.95–5.45, 5.70–6.25, 6.77, 7.10, 7.27.

EXAMPLE 51

2-(5-Hexenylamino)-6-benzothiazolol (Formula C-3: A, B and D are H; Y is (CH$_2$)$_n$; n is 4; Z is CH=CH$_2$)

The 6-Tetrahydropyran-2-oxy(5-hexenylamino)benzothiazole compound (2.0 g) is dissolved in acetic acid (5 ml) and water (2 ml), then stirred overnight at room temperature. Removal of the solvent leaves a clear oil which is chromatographed over silicon dioxide (75 g). Elution with dichloromethane, then 1.5% methanol/trichloromethane gives the title product which is recrystallized from chloroform as white crystals, mp 92°–94° C., (0.58 g).

Physical characteristics are as follows:
Analysis Found: C, 62.90; H, 6.55; N, 11.21; S, 12.63.
Mass Spec (m/e): 249, 248, 193, 180, 179, 167, 166, 152, 151.
Infra Red (cm$^{-1}$, $\nu_{max}$): 3309, 3048, 2658, 2574, 1640, 1609, 1592, 1565, 1233, 1218, 1192, 1054, 906, 846, 813, 605.
UV ($\lambda$, Ethanol): 224, 271, 305, 313.
NMR ($\delta$, D$_4$-Methanol): 1.20–1.85, 1.85–2.25, 3.33, 4.60–5.15, 5.50–6.05, 6.70, 6.98, 7.22.

EXAMPLE 52

2-(5-Hexenylamino)-6-benzothiazolol Maleic Acid Salt (Formula C-3: A, B and D are H; Y is (CH$_2$)$_n$; n is 4; Z is CH=CH$_2$)

2-(5-Hexenylamino)-6-benzothiazolol (100 mg) and maleic acid (47 mg) are stirred at 25° C. in tetrahydrofuran for 4 hr. Removal of the solvent and recrystallization from acetone gives white crystals, mp 136°–137.5° C., (100 mg) of the title compound.

Physical characteristics are as follows:
Analysis Found: C, 56.00; H, 5.46; N, 7.79; S, 8.83.
Mass Spec (m/e): 249, 248, 180, 179, 166, 152, 72.
Infra Red (cm$^{-1}$, $\nu_{max}$): 3129, 3077, 2397, 1830, 1649, 1615, 1571, 1552, 1291, 1277, 1241, 1219, 1170, 1130, 1123, 1102, 909, 883, 865, 847, 785, 757, 678, 652.
UV ($\lambda$, Ethanol): 222, 272, 305, 316.

EXAMPLE 53

2-[(5-Bromohexyl)amino]-6-benzothiazolol (Formula C-3: A, B and D are H; Y is (CH$_2$)$_n$; n is 4; Z is CHBrCH$_3$)

6-Methoxy-2[(5-hexenyl)amino]benzothiazole (1.0 g) is dissolved, under nitrogen, in dichloromethane (20 ml) and cooled to −78° C. A 1M solution (13 ml) of boron tribromide is added via a syringe and the solution allowed to come to room temperature over 2 hr. The mixture is then slowly added to saturated sodium dicarbonate (25 ml) and extracted with three 25 ml portions of trichloromethane. The organic extracts are dried (sodium sulfate), filtered and evaporated, leaving a white solid (350 mg). A sticky semi-solid is filtered from the aqueous layer. The combined solids are chromatographed over silicon dioxide (100 g) eluting with 1% methanol/dichloromethane to yield the product. Recrystallization from acetone-Skellysolve B gives short white needles, mp 136°–138° C., (540 mg) of the title compound.

Physical characteristics are as follows:
Analysis Found: C, 47.90; h, 5.37; N, 8.62; S, 9.61.
Mass Spec (m/e): 330, 328, 249, 248, 233, 219, 205, 180, 179, 166, 52.
Infra Red (cm$^{-1}$, $\nu_{max}$): 3309, 3048, 2657, 2570, 1610, 1591, 1565, 1273, 1235, 1218.
UV ($\lambda$, Ethanol): 224, 271, 305.
NMR ($\delta$, D$_6$-Acetone): 1.10–2.05, 3.43, 4.16, 6.74, 7.07, 7.26.

EXAMPLE 54

2-[[5-(4-Methylphenyl)hexyl]amino]-6-benzothiazolol (Formula C-3: A, B and D are H; Y is (CH$_2$)$_n$; n is 4; Z is CH(CH$_3$)p-tolyl)

6-Methoxy-2-[(5-hexenyl)amino]benzothiazole (1.0 g) is dissolved in toluene (40 ml) and aluminum chloride (1.02 g) added. The mixture is refluxed for 2 hr then cooled and 1N hydrochloric acid (20 ml) added. The solvents are decanted from the white gum which is stirred overnight with saturated sodium bicarbonate (25 ml). A semi-solid is filtered and chromatographed over silicon dioxide (100 g). Elution with dichloromethane then 2% methanol/dichloromethane gives a clear glass which crystallizes on cooling. Recrystallication from acetone-Skellysolve B gives white prisms, mp 139°–143° C., (0.21 g) of the title compound.

Physical characteristics are as follows:
Analysis Found: C, 70.48; H, 7.52; N, 8.20; S, 9.30.
Mass Spec (m/e): 341, 340, 221, 208, 179, 178, 166, 152, 119.
Infra Red (cm$^{-1}$, $\nu_{max}$): 3301, 1603, 1565, 1552, 1236, 1223, 1215, 842, 817, 607.
UV ($\lambda$, Ethanol): 223, 272, 305, 313.
NMR ($\delta$, D$_6$-Acetone): 0.75–1.60, 1.97, 2.27, 2.73, 3.08, 6.46, 6.74, 6.78, 6.97.

EXAMPLE 55

6-[(6-Hydroxy-2-benzothiazolyl)amino-1-(4-methylphenyl)-1-hexanone, (Formula C-3: A, B and D are H; Y is (CH$_2$)$_n$; n is 5; Z is p-toluyl) and 6-[(6-hydroxy-2-benzothiazolyl)aminohexanoic acid methyl ester (Formula C-3: A, B and D are H; Y is (CH$_2$)$_n$; n is 5; and Z is COOCH$_3$)

6-[(6-Methoxy-2-benzothiazolyl)amino]hexanoic acid methyl ester (4.45 g) is dissolved with warming in toluene (200 ml) and aluminum chloride (3.85 g) added. The reaction is heated under reflux for 2 hr when TLC indicates that more than 50% of the starting material remains. More aluminum chloride (3.85 g) is added and refluxing continued for 2 hr at which time the reaction is cooled and treated with 1N hydrochloric acid (100 ml). The solvents are decanted from the gum which separates and the gum stirred in saturated sodium bicarbonate (100 ml) for 1 hr. The resultant semi-solid is filtered and chromatographed over silicon dioxide (450 g) in a medium pressure column eluting with 2% methanol/trichloromethane at 20 psi and 17 ml/min. Hexahydro-1-(6-hydroxy-2-benzothiazolyl)-2H-azepinone is eluted as the first component (480 mg) and recrystallized from acetone as a white solid, mp 195.5°–197.5° C.

The p-tolyl title compound is eluted next but is contaminated with the hydroxy ester (1.3 g). The mixture is rechromatographed over silicon dioxide (150 g) in a medium pressure column at 15 psi and 17 ml/min eluting with 1% methanol/trichloromethane. The p-tolyl title compound is obtained pure (320 mg) and recrystalized from acetone as pale yellow prisms, mp 159°–161.5° C.

Physical characteristics are as follows:
Analysis Found: C, 67.62; H, 6.13; N, 7.71; S, 8.72.

Mass Spec (m/e): 355, 354, 235, 221, 193, 179, 166, 152, 119, 91.

Infra Red (cm$^{-1}$, $\nu_{max}$): 3327, 1670, 1632, 1597, 1567, 1292, 1239, 1178, 971, 842, 804.

UV ($\lambda_{max}$, Ethanol): 217, 224, 259, 305.

NMR ($\delta$, D$_6$-DMSO): 1.10–1.85, 2.38, 2.75–3.10, 3.10–3.45, 6.64, 7.02, 7.16, 7.27, 7.58, 7.82, 9.04.

The hydroxy ester title compound is eluted pure in the ester fractions off the column and recrystallized from acetone as a white solid, mp 194°–196° C., (650 mg).

Physical characteristics are as follows:

Analysis Found: C, 57.12; H, 6.17; N, 9.32; S, 10.43.

Mass Spec (m/e): 294, 235, 221, 193, 180, 179, 166, 152, 151.

Infra Red (cm$^{-1}$, $\nu_{max}$): 3371, 2766, 2738, 2598, 1721, 1608, 1597, 1549, 1547, 1516, 1281, 1261, 1248, 1237, 1219, 1209, 1193, 1177, 1058, 976, 875, 846, 805, 630.

UV ($\lambda$, Ethanol): 223, 270, 305, 311.

NMR ($\delta$, D$_6$-DMSO): 1.00–1.75. 2.25, 3.20, 3.57, 6.55, 6.93, 7.08, 7.48, 8.97.

EXAMPLE 56

6-(5-Hexenyloxy)benzothiazolol (Formula D-3: A, B and D are H; C is hydroxy; E is 5; Y is (CH$_2$)$_n$; n is 4; Z is CH=CH$_2$) (Refer to Chart D)

A 50% oil dispersion of sodium hydride (0.40 g) is washed with three 7 ml portions of hexane, then treated with dry tetrahydrofuran (20 ml) and 5-hexen-1-ol (0.80 g). After 1 hour stirring, 6-tetrahydropyranyl-2-oxy-2-chlorobenzothiazole (1.0 g) is added and the mixture refluxed for 4 hours then 2 days at room temperature. Water (2 ml) is added and the solvent evaporated to yield an oil which is dissolved in trichloromethane (25 ml). The organic extract is washed with water (25 ml), brine (25 ml), dried with sodium sulfate and evaporated to yield the crude tetrahydropyranyl adduct as an oil. The oil is dissolved in acetic acid (10 ml) and water (2 ml) then stirred overnight. The precipitated solid (0.80 g, 86%) is filtered, dried and recrystallized from chloroform as white crystals, to yield the title product, mp 120°–121.5° C. (0.70 g).

Physical characteristics are as follows:

Analysis Found: C, 62.34; H, 5.98; N, 5.43; S, 12.77.

Mass Spec (m/e): 249, 168, 167, 166, 139, 122, 55.

Infra Red (cm$^{-1}$, $\nu_{max}$): 3087, 3066, 2588, 1640, 1612, 1547, 1297, 1284, 1259, 1238, 1226, 1216, 1193, 1061, 1026, 1005, 907, 854, 846, 825, 760, 691, 641.

UV ($\lambda$, Ethanol): 218, 221, 258, 293, 302.

NMR ($\delta$, D$_6$-acetone): 1.30–2.30, 4.50, 4.80–5.15, 5.55–6.10, 6.88, 7.20, 7.45, 8.52.

EXAMPLE 57

2-[[3-(Diethylamino)propyl]amino]-6-benzothiazolol dihydrochloride and its compound with Hydroquinone (Formula C-3: A, B and D are H; Y is (CH$_2$)$_n$; n is 3; Z is N(CH$_2$CH$_3$)$_2$) (Refer to Chart C)

1,4-Benzoquinone (5.7 g) is dissolved in hot ethanol (85 ml) and added dropwise to a stirred solution of 1-(3-diethylaminopropyl)-2-thiourea (5.0 g) in ethanol (50 ml) and concentrated hydrochloric acid (4.6 ml). The mixture is stirred at room temperature for 18 hours during which time a pale yellow solid precipitates. The title compound with hydroquinone is collected by filtration and washed with two 25 ml portions of ethanol and dried (1.1 g). Additional title product with hydroquinone is isolated from the filtrate after reducing the volume to 25–30 ml (3.5 g), mp 198°–200° C.

Physical characteristics are as follows:

Analysis Found: C, 51.60; H, 6.20; N, 9.14; S, 6.92; Cl, 15.39.

Mass Spec (m/e): 279, 209, 193, 179, 178, 110, 86, 84, 72, 36.

Infra Red (cm$^{-1}$, $\nu_{max}$): 3104, 3216, 2709, 1627, 1612, 1591, 1519, 1254, 1228, 1204, 866, 846, 813, 762, 628.

NMR ($\delta$, D$_6$-DMSO): 1.26, 2.12, 2.85–3.45, 3.72, 6.64, 6.98, 7.38, 7.53, 8.77, 10.50, 10.97.

The hydroquinone dihydrochloride salt of the title compound (1.0 g) is dissolved in water (10 ml) and neutralized with 5% sodium bicarbonate and extracted with three 25 ml portions of ethyl acetate. The combined extracts are washed with water (25 ml), dried (sodium sulfate) and the solvent removed leaving a hard glass (0.77 g). The glass is chromatographed over silicon dioxide (100 g) eluting with 5% methanol/dichloromethane. The first component eluted is hydroquinone and then the title product is eluted with 5% methanol/dichloromethane and 1% triethylamine and crystallized twice from acetone as a white powder (0.28 g) mp 136°–137.5° C.

Physical characteristics are as follows:

Analysis Found: C, 59.55; H, 7.70; N, 14.82; S, 11.45.

Mass Spec (m/e): 279, 208, 193, 179, 178, 152, 86, 84, 72, 58.

Infra Red (cm$^{-1}$, $\nu_{max}$): 3223, 3126, 2656, 2571, 1616, 1573, 1240, 1226, 1216, 1192, 1153, 1142, 1118, 1080, 1044, 985, 831, 803, 744, 684, 611.

UV ($\nu_{max}$): 224, 271, 305, 314.

NMR ($\delta$, D$_4$-Methanol): 1.02, 1.55–2.05, 2.35–2.75, 3.20–3.50, 6.70, 6.98, 7.22.

EXAMPLE 58

2-[[3-(Diethylamino)propyl]amino]-6-benzothiazolol Dihydrochloride (Formula C-3: A, B and D are H; Y is (CH$_2$)$_n$; n is 3; Z is N(CH$_2$CH$_3$)$_2$)

2-[[3-(Diethylamino)propyl]amino-6-benzothiazolol (0.34 g) in a 4:1 mixture of dichloromethane/methanol (10 ml) is cooled to 0° C. and treated with anhydrous hydrogen chloride for five minutes and then allowed to warm to room temperature. Removal of the solvent leaves a pale tan solid which is recrystallized twice from methanol/acetone with a Darco treatment to give fine white needles (0.21 g), mp 234°–236° C. of the title compound.

Physical characteristics are as follows:

Analysis Found: C, 47.38; H, 6.49; N, 11.81; S, 9.45; Cl, 20.21.

Mass Spec (m/e): 279, 208, 193, 179, 178, 152, 86, 84.

Infra Red (cm$^{-1}$, $\nu_{max}$): 3426, 3388, 2762, 2656, 1634, 1608, 1232, 836, 812.

UV ($\nu_{max}$): 223, 272, 303, 311.

EXAMPLE 59

6-[[6-[(3-Carboxy-1-oxopropyl)amino]-2-benzothiazolyl]thio]hexanoic acid methyl ester (Formula A-3: A, B and D are H; C is 4-amino-4-oxobutanoic acid; E is S; Y is (CH$_2$)$_n$; n is 5; Z is COOCH$_3$)

Succinic acid (0.187 g) is added to 6-[[6-amino]-2-benzothiazolyl]thio]hexanoic acid methyl ester (0.58 g) in acetonitrile (25 ml) and the solution heated at reflux for 3 hrs and then cooled to 0° C. A white precipitate is collected by filtration and washed with acetonitrile (5 ml) and dried. Recrystallization from acetone and then acetonetrichloromethane gives fine fluffy needles, mp 148°–149.5° C. (0.51 g) of the title compound.

Physical characteristics are as follows:

Analysis Found: C, 52.27; H, 5.68; N, 6.77; S, 15.90

Mass Spec (m/e): 345, 310, 264, 183, 182, 181, 69, 55, 41, 28.

Infra Red (cm$^{-1}$, $\nu_{max}$): 3333, 3219, 1749, 1734, 1726, 1673, 1605, 1582, 1538, 1292, 1266, 1210, 1190, 1170, 1132, 1021, 1004, 965, 855, 822, 716, 628.

UV ($\lambda_{max}$, Ethanol): 224, 296, 301, 313.

NMR, ($\delta$, DMSO): 1.15–1.90, 2.30, 2.40–2.65, 3.30, 3.57, 7.48, 7.74, 8.35, 10.14.

EXAMPLE 60

6-[[6-[(3-Carboxy-1-oxopropyl)amino]-2-benzothiazolyl]thio]hexanoic acid methyl ester, tromethamine salt 6-[[6-[(3-Carboxy-1-oxopropyl)amino]-2-benzothiazolyl]thio]hexanoic acid methyl ester (0.25 g) and tromethamine (0.074 g, 0.61 mmoles) are dissolved in methanol (5 ml) and stirred at room temperature for 3 hrs. Removal of the solvent leaves a white solid that crystallizes from methanol-ethyl acetate giving clear prisms, mp 138°–139.5° C. (0.25 g) of the title compound.

Physical characteristics are as follows:

Analysis Found: C, 49.74; H, 6.31; N, 7.95; S, 12.29.

Mass Spec (m/e): 410, 392, 311, 310, 264, 263, 183, 182, 69, 55, 28.

Infra Red (cm$^{-1}$, $\nu_{max}$): 3470, 3355, 3165, 2109, 1708, 1681, 1608, 1585, 1536, 1267, 1224, 1194, 1182, 1063, 1040, 1034, 1023, 866.

UV ($\lambda_{max}$, Ethanol): 224, 298, 301, 312.

FORMULA CHART

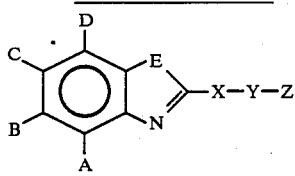

I

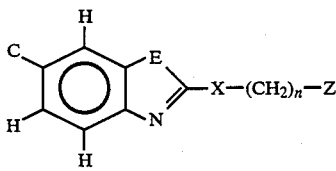

II

CHART A

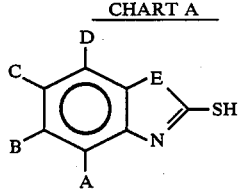

A-1

+

R$_1$—Y—Z

A-2

CHART A -continued

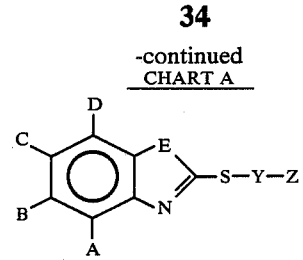

A-3

CHART B

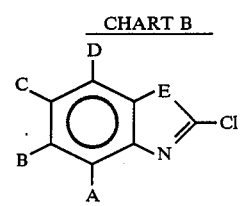

B-1

+

H$_2$N—Y—Z

B-2

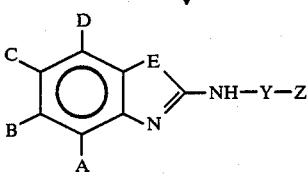

B-3

CHART C

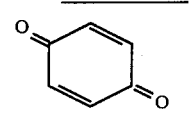

C-1

+

C-2

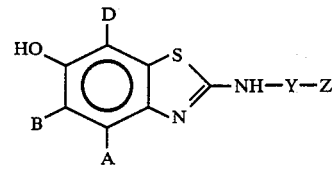

C-3

CHART D

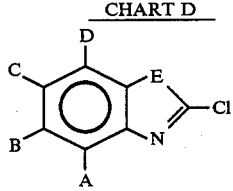

D-1

+

HO—Y—Z

D-2

-continued
CHART D

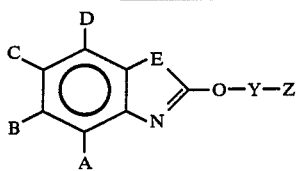

D-3

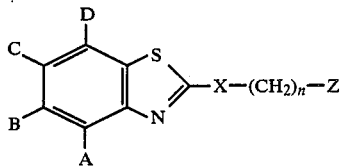

What is claimed is:
1. A compound according to the structural formula

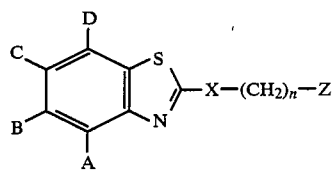

wherein A, B, C and D are independently hydrogen or hydroxy provided that they are all not hydrogen;
X is O, S or NH; and
Z is
(1) exo or endo 2-norbornyl,
(2) 1-adamantyl,
(3) 3-cyclohexenyl,
(4) 2-cyclohexanolyl,
(5) 2-cyclohexanone,
(6) Cl,
(7) Br,
(8) CN,
(9) OCOCH$_3$,
(10) COOCH$_3$,
(11) C≡CH,
(12) CH=CH$_2$,
(13) CH=CH(C$_1$-C$_4$)alkyl,
(14) CH=CH-phenyl,
(15) CH(Br)CH$_3$,
(16) CH(CH$_3$)phenyl,
(17) CH(CH$_3$)$p$-tolyl,
(18) phenyl unsubstituted or substituted at the 4 position with bromine or COOCH$_3$;
(19) benzoyl,
(20) toluyl,
(21) 2-naphthyl,
(22) 9-anthracenyl,
(23) 2-tetrahydrofuranyl,
(24) phthalimido,
(25) 2-benzimidazolyl,
(26) 2-mercapto-6-hydroxybenzothiazolyl, or
(27) 7-methoxy-coumarin-4-yl; and pharmaceutically acceptable salts thereof; wherein n is 4–11, except when Z is:
(a) exo or endo 2-norbornyl,
(b) 1-adamantyl,
(c) 3-cyclohexenyl,
(d) 2-cyclohexanolyl, or
(e) 2-cyclohexanone; then n is 0.
2. The compound of claim 1 according to the structural formula:

wherein A, B and D are hydrogen;
C is hydroxy;
X is
(1) S, or
(2) NH;
n is 4–11;
Z is
(1) CH=CH$_2$, or
(2) COOCH$_3$; and pharmaceutically acceptable salts thereof.
3. A compound according to claim 1 wherein the compound is:
Hexanoic acid, 6-[(6-hydroxy-2-benzothiazolyl)thio]-, methyl ester;
Hexanenitrile, 6-[(6-hydroxy-2-benzothiazolyl)thio]-;
6-Benzothiazolol, 2-(5-hexenylthio)-;
6-Benzothiazolol, 2-(bicyclo[2.2.1]hept-2-ylthio)-;
6-Benzothiazolol, 2-[(2-hydroxycyclohexyl)thio]-;
4-Benzothiazolol, 2-(5-hexenylthio)-;
Hexanoic acid, 6-[(4-hydroxy-2-benzothiazolyl)thio]-, methyl ester;
6-Benzothiazolol, 2-[(6-bromohexyl)thio]-;
Pentanol, 5-[(6-hydroxybenzothiazol-2-yl)thio]-acetate-;
Benzothiazole-6-ol, 2-[(2-oxocyclohexyl)thio]-;
6-Benzothiazolol, 2-(b 2-cyclohexenylthio)-;
2-[6-[(6-Hydroxy-2-benzothiazolyl)thio]hexyl]-1H-Isoindole-1,3(2H)dione;
6-[(6-Hydroxy-2-benzothiazolyl)amino]hexanoic acid methyl ester;
2-[(5-Bromohexyl)amino]-6-benzothiazolol;
2-[[5-(4-Methylphenyl)hexyl]amino]-6-benzothiazolol;
2-(b 5-Hexenylamino)-6-benzothiazolol;
2-(5-Hexenylamino)-6-benzothiazolol maleic acid salt;
6-Benzothiazolol, 2-[(6-chlorohexyl)thio]-2-(Tricyclo[3.3.1.1.3,7]dec-1-ylamino)-6-benzothiazolol;
6-[(6-Hydroxy-2-benzothiazolyl)amino]-1-(4-methylphenyl)-1-hexanone;
Endo-2-(bicyclo[2.2.1]hept-2-ylamino)-6-benzothiazolol;
2-(5-Hexenyloxy)-6-benzothiazolol; or.
4. A compound according to claim 2 wherein the compound is:
Hexanoic acid, 6-[(6-hydroxy-2-benzothiazolyl)thio]-, methyl ester;
6-Benzothiazolol, 2-(5-hexenylthio)-;
6-[(6-Hydroxy-2-benzothiazolyl)amino]hexanoic acid methyl ester;
2-(5-Hexenylamino)-6-benzothiazolol;
2-(5-Hexenylammino)-6-benzothiazolol maleic acid salt.
5. A compound selected from the group consisting of:
2-[[3-(Diethylamino)propyl]amino]-6-benzothiazolol;
2-[[3-(Diethylamino(propyl]amino]-6-benzothiazolol, hydroquinone dihydrochloride salt;
2-[[3-(Diethylamino(propyl]amino]-6-benzothiazolol dihydrochloride.

* * * * *